(12) United States Patent
Hudyma et al.

(10) Patent No.: US 6,486,159 B2
(45) Date of Patent: Nov. 26, 2002

(54) WATER SOLUBLE PRODRUGS OF AZOLE COMPOUNDS

(75) Inventors: Thomas W. Hudyma, Durham, CT (US); Oak K. Kim, Guilford, CT (US); Xiaofan Zheng, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/789,986

(22) Filed: Feb. 21, 2001

(65) Prior Publication Data

US 2001/0039353 A1 Nov. 8, 2001

Related U.S. Application Data

(62) Division of application No. 09/315,606, filed on May 20, 1999, now Pat. No. 6,265,584.
(60) Provisional application No. 60/103,560, filed on Oct. 7, 1998, and provisional application No. 60/086,435, filed on May 22, 1998.

(51) Int. Cl.[7] ............... A61K 31/4178; A61K 31/4436; C07D 413/14; C07D 417/06; C07D 417/14
(52) U.S. Cl. ............. 514/252; 514/365; 544/364; 548/204; 548/266.2; 548/266.6; 548/268.6
(58) Field of Search ............... 544/364; 548/204, 548/266.2, 266.6, 268.6; 514/252, 365

(56) References Cited

U.S. PATENT DOCUMENTS

| | | | |
|---|---|---|---|
| 5,648,372 A | 7/1997 | Naito et al. | 514/383 |
| 5,661,151 A | 8/1997 | Saksena et al. | 514/252 |
| 5,707,977 A | 1/1998 | Heeres et al. | 514/85 |
| 6,265,584 B1 * | 7/2001 | Hudyma et al. | 548/203 |
| 6,359,141 B2 * | 3/2002 | Hudyma et al. | 548/205 |

FOREIGN PATENT DOCUMENTS

| | | |
|---|---|---|
| EP | 829478 A2 | 3/1998 |
| WO | WO 97/28169 | 8/1997 |

OTHER PUBLICATIONS

H. Bundgaard, et al, J. Med. Chem., 32(12), pp. 2503–2507, 1989.
E. Jensen, et al, Int. J. Pharmaceut., 58, pp. 143–153, 1990.
H. Bundgaard, Drugs of the Future, 16(5), pp. 443–458, 1991.

* cited by examiner

Primary Examiner—Flona T. Powers
(74) Attorney, Agent, or Firm—David M. Morse

(57) ABSTRACT

Water-soluble prodrugs of triazole antifungal compounds having a secondary or tertiary hydroxy group are provided. More particularly, new water-soluble triazole antifungal compounds are provided having the general formula

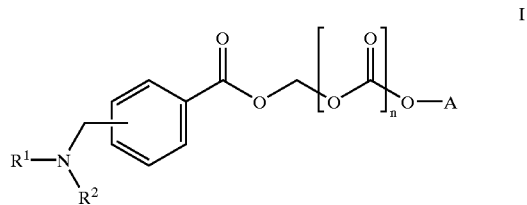

wherein A is the non-hydroxy portion of a triazole antifungal compound of the type containing a secondary or tertiary hydroxyl group and n, $R^1$ and $R^2$ are as defined in the specification.

17 Claims, No Drawings

WATER SOLUBLE PRODRUGS OF AZOLE COMPOUNDS

CROSS-REFERENCE TO RELATED APPLICATIONS

This application is a divisional of application Ser. No. 09/315,606, filed May 20, 1999, now U.S. Pat. No. 6,265,584, which claims the benefit of provisional application No. 60/103,560, filed Oct. 7, 1998 and provisional application No. 60/086,435, filed May 22, 1998.

BACKGROUND OF THE INVENTION

This invention relates to a new class of azole derivatives, methods for their use, and processes for their production. The compounds described herein are useful for the treatment of fungal infections in humans and other mammals. The present invention provides a compound represented by the general formula

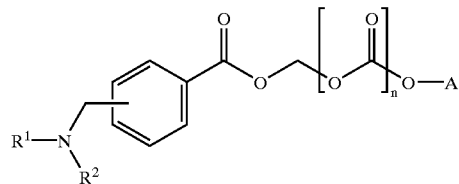

I wherein A is the non-hydroxy portion of a triazole antifungal compound of the type containing a secondary or tertiary hydroxy group, n is 0 or 1, and $R^1$ and $R^2$ are hydrogen, $C_1–C_6$ alkyl or $C_2–C_6$ alkenyl, said alkyl or alkenyl group being optionally substituted by a hydroxy or dimethylamino group, or $R^1$ and $R^2$ taken together with the nitrogen to which they are attached forms a heterocyclic group of the formula

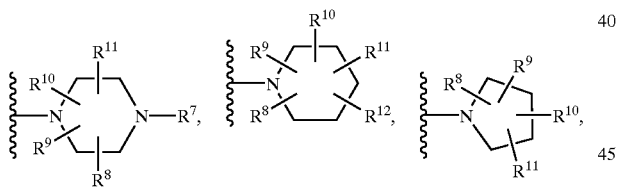

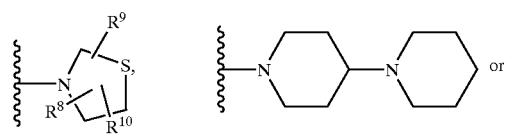

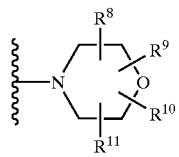

where $R^7$ is hydrogen, CHO, $COR^{13}$ or $C_1–C_6$ alkyl in which the alkyl group may be optionally interupted by an oxygen atom or $NR^{14}$ and may be substituted by hydroxy, $R^8$, $R^9$, $R^{10}$, $R^{11}$ and $R^{12}$ are each independently hydrogen, hydroxy, $CONH_2$, or $C_1–C_6$ alkyl, said alkyl group being optionally substituted by hydroxy, $R^{13}$ is $C_1–C_6$ alkyl and $R^{14}$ is hydrogen or $C_1–C_6$ alkyl; or a pharmaceutically acceptable salt thereof.

DESCRIPTION OF THE PRIOR ART

Triazole antifungal compounds are well known in the prior art. Of the several classes known, one particularly potent class contains a tertiary hydroxyl group. For example, U.S. Pat. No. 5,648,372 discloses that (2R,3R)-3-[4-(4-cyanophenyl)thiazol-2-yl]-2-(2,4-difluorophenyl)-1-(1H-1,2,4-triazol-1-yl)-butan-2-ol has anti-fungal activity.

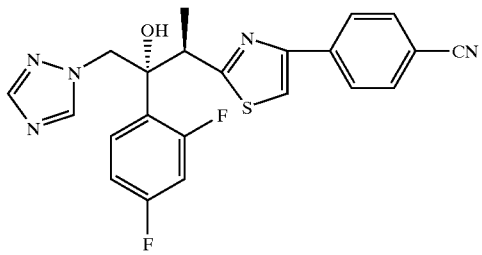

The utility of this class of compounds is limited by their low water solubility. One method of addressing this problem was disclosed in European Patent Application 829478, where the water solubility of an azole antifungal agent was increased by attaching a linked amino-acid to the azole portion of the molecule.

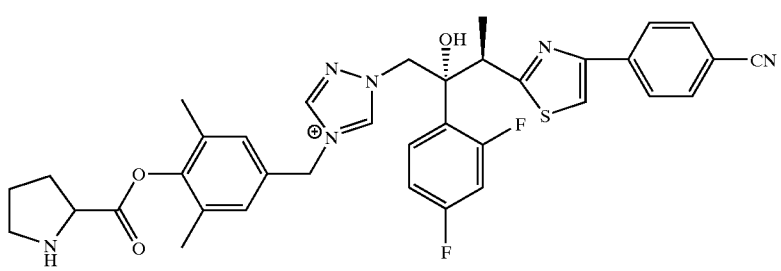

Alternatively, WO 97/28169 discloses that a phosphate moiety can be attached directly to the tertiary hydroxyl portion of the anti-fungal compound, e.g. the compound having the formula

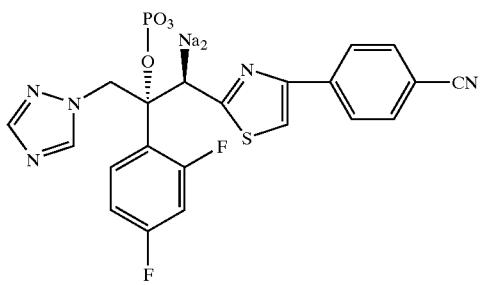

Examples describing the use of N-N-dialkylaminomethyl benzoate derivatives as prodrugs can be found in H. Bundgaard et al, J. Med Chem. 32, 2503 (1989); E. Jensen et. al. Int. J. Pharmaceut. 58,143 (1990); and H. Bundgaard, Drugs of the Future 16, 443 (1991).

SUMMARY OF THE INVENTION

It has now been found that triazole anti-fungal compounds containing a secondary or tertiary hydroxyl group, including (2R,3R)-3-[4-(4-cyanophenyl)thiazol-2-yl]-2-(2,4-difluorophenyl)-1-(1H-1,2,4-triazol-1-yl)-butan-2-ol, may be converted into prodrugs with superior properties to those previously disclosed by attaching an amino-containing moiety via a linking group. Specifically, the invention covers compounds of the formula:

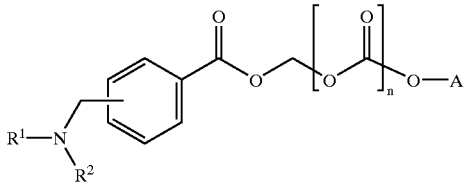

wherein A is the non-hydroxy portion of a triazole antifungal compound of the type containing a secondary or tertiary hydroxy group, n is 0 or 1, and $R^1$ and $R^2$ are hydrogen, $C_1$–$C_6$ alkyl or $C_2$–$C_6$ alkenyl, said alkyl or alkenyl group being optionally substituted by a hydroxy or dimethylamino group, or $R^1$ and $R^2$ taken together with the nitrogen to which they are attached forms a heterocyclic group of the formula

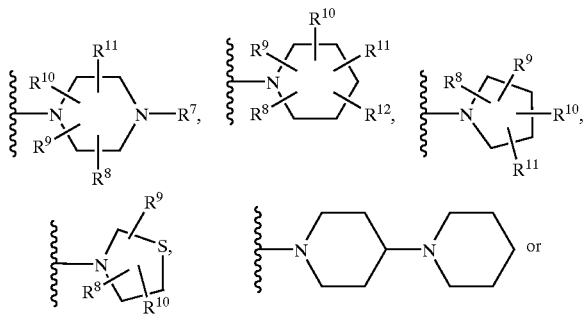

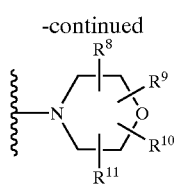

where $R^7$ is hydrogen, CHO, $COR^{13}$ or $C_1$–$C_6$ alkyl in which the alkyl chain may be optionally interupted by either an oxygen atom or $NR^{14}$ and may be substituted by a hydroxy group, $R^8$, $R^9$, $R^{10}$, $R^{11}$ and $R^{12}$ are each independently hydrogen, hydroxy, $CONH_2$ or $C_1$–$C_6$ alkyl, said $R^8$, $R^9$, $R^{10}$, $R^{11}$ or $R^{12}$ alkyl group being optionally substituted by hydroxy, $R^{13}$ is $C_1$–$C_6$ alkyl and $R^{14}$ is hydrogen or $C_1$–$C_6$ alkyl; or a pharmaceutically acceptable salt thereof.

In a preferred embodiment, A represents the non-hydroxy portion of a triazole antifungal compound of the type containing a tertiary hydroxy group.

The various methylamine substituents of formula I may be attached in either an ortho, meta, or para relationship to the ester substituent, with the preferred attachment being either meta or para.

In a preferred embodiment A can be

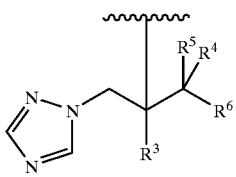

wherein $R^3$ represents phenyl substituted by one or more (preferably 1–3) halogen atoms;

$R^4$ represents H or $CH_3$;

$R^5$ represents H, or taken together with $R^4$ may represent $=CH_2$;

$R^6$ represents a 5- or 6 membered nitrogen containing ring which may be optionally substituted by one or more groups selected from halogen, =O, phenyl substituted by one or more groups selected from CN, $(C_6H_4)$— $OCH_2CF_2CHF_2$ and $CH=CH-(C_6H_4)$— $OCH_2CF_2CHF_2$, or phenyl substituted by one or more groups selected from halogen and methylpyrazolyl.

Nitrogen containing heterocycles which $R^6$ may represent include triazolyl, pyrimidinyl, and thiazolyl.

Specific examples of A include, but are not limited to, the following:

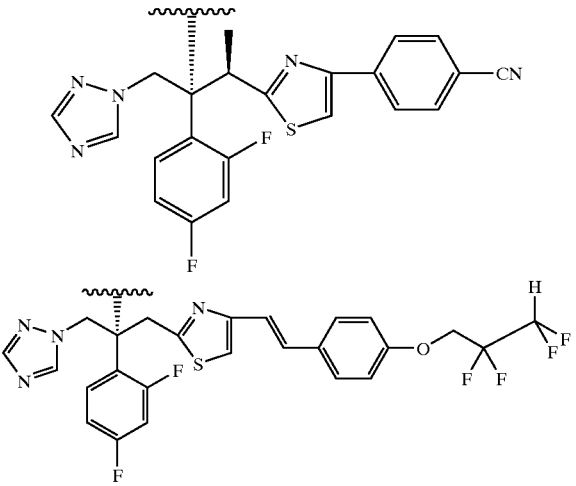

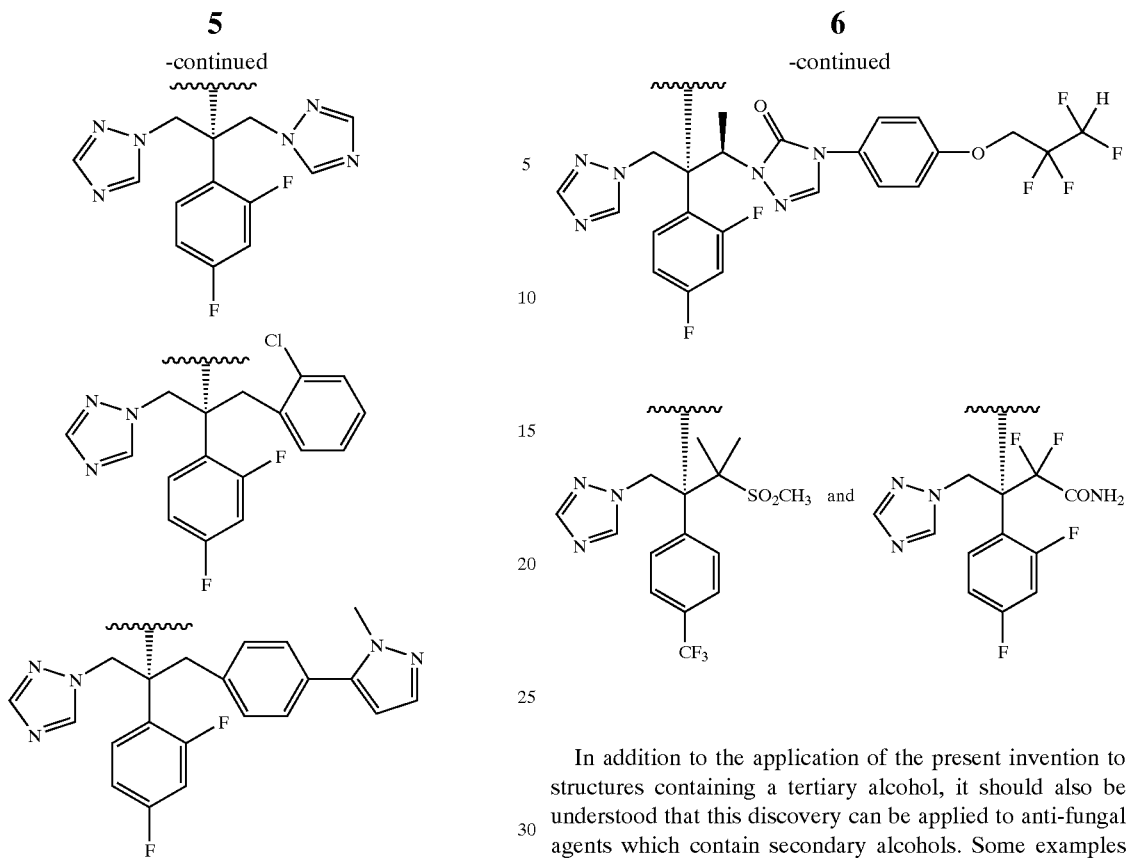
In addition to the application of the present invention to structures containing a tertiary alcohol, it should also be understood that this discovery can be applied to anti-fungal agents which contain secondary alcohols. Some examples include, but are not limited to, the following:
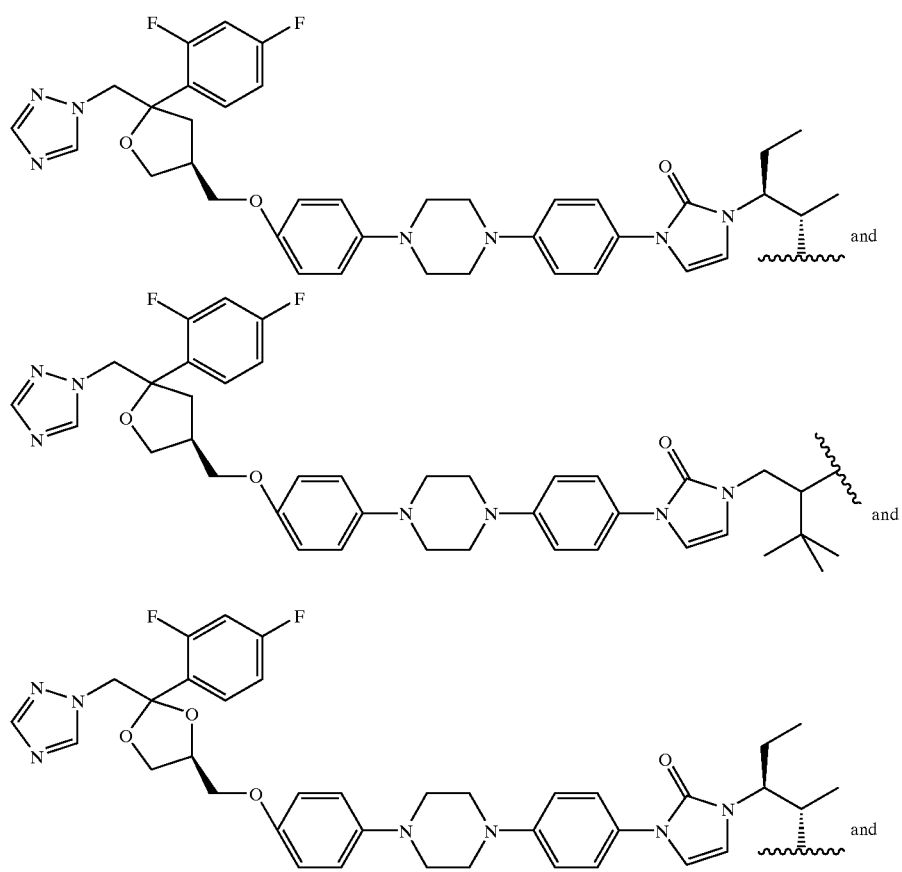

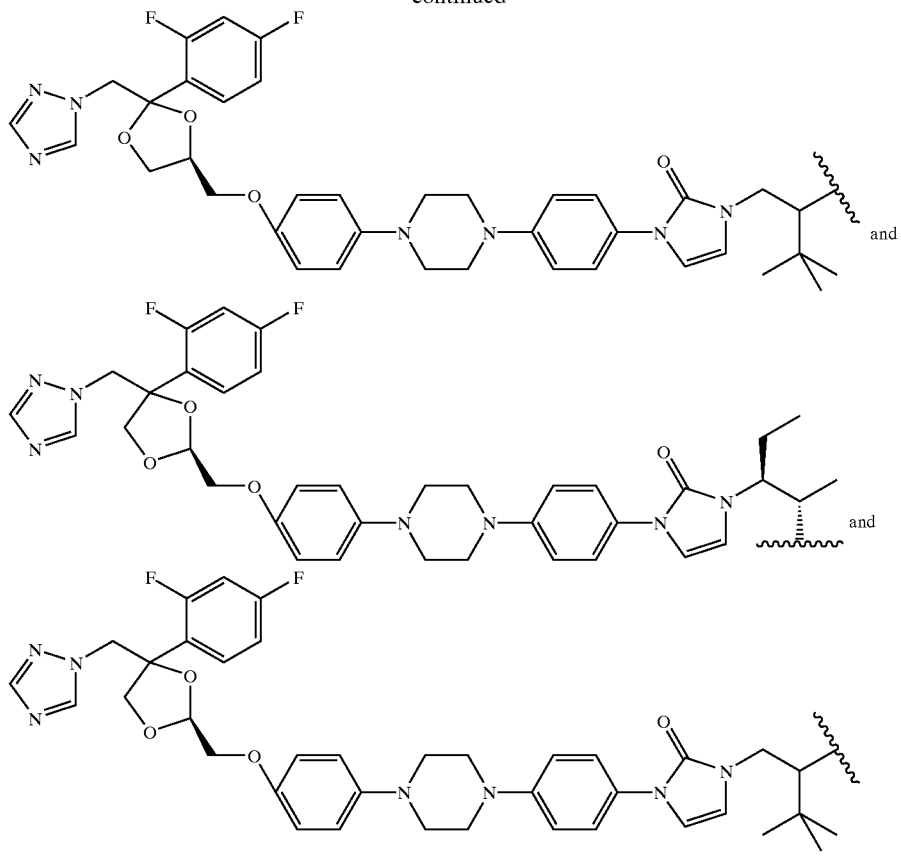
Representative $R^1$, $R^2$ and n values are shown below:
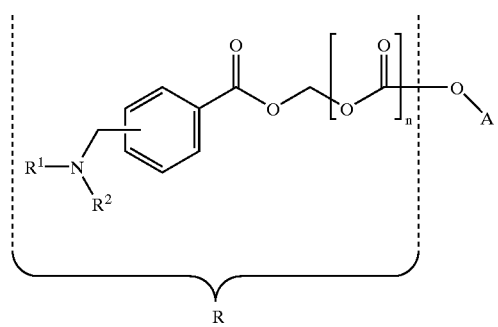
(where A represents the non-hydroxy portion of a triazole anti-fungal compound of the type containing a tertiary or secondary hydroxyl group)
| R |
|---|
| 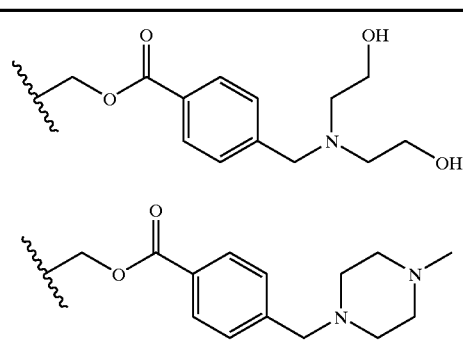 |
| R |
|---|
| 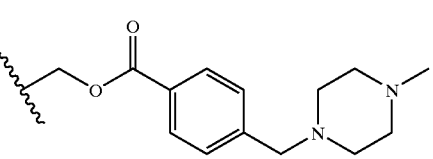 |
| 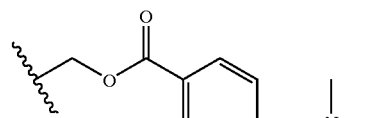 |
| 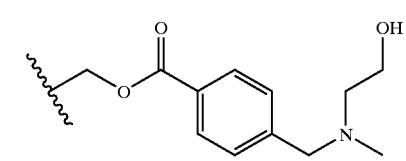 |

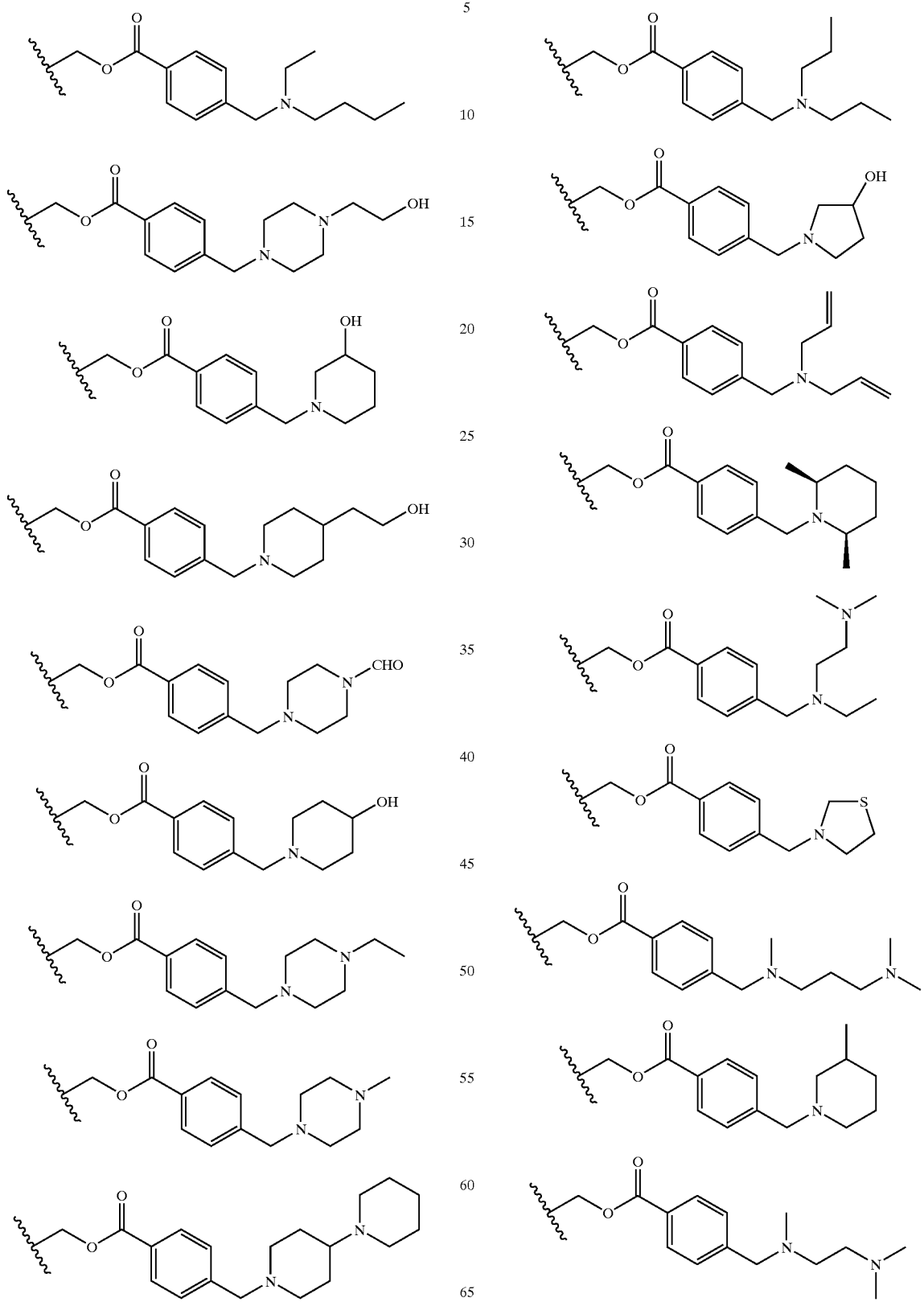

| -continued |
| --- |
| R |
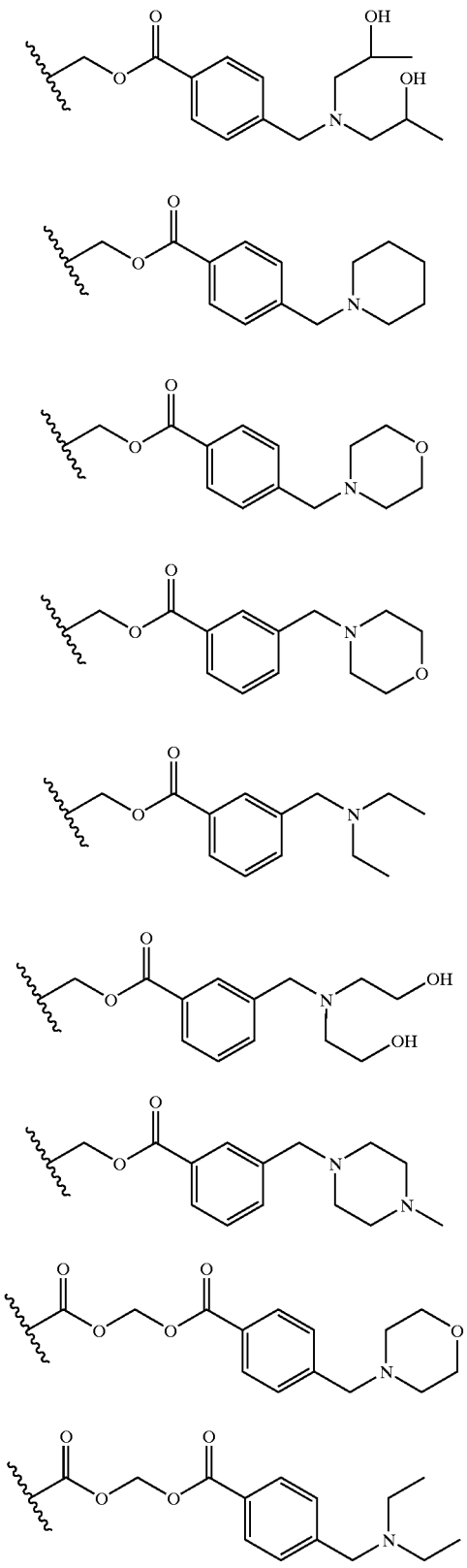
| -continued |
| --- |
| R |
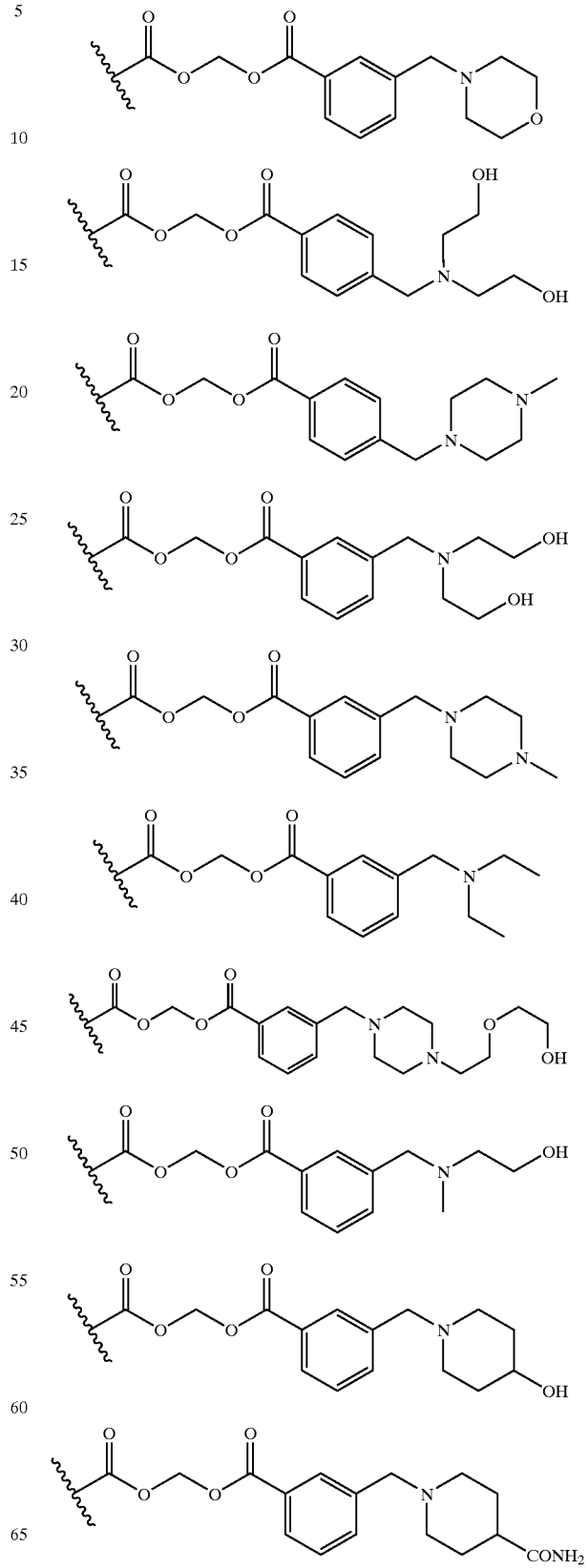

-continued

R

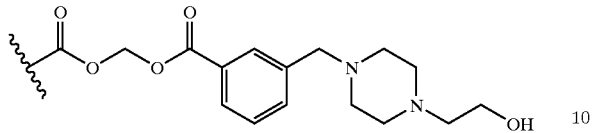

DEFINITIONS

The term "pharmaceutically acceptable salt" as used herein is intended to include the non-toxic acid addition salts with inorganic or organic acids, e.g. salts with acids such as hydrochloric, phosphoric, sulfuric, maleic, acetic, citric, succinic, benzoic, fumaric, mandelic, p-toluene-sulfonic, methanesulfonic, ascorbic, lactic, gluconic, trifluoroacetic, hydroiodic, hydrobromic, and the like.

The term "halogen" includes chloro, bromo, fluoro and iodo, and is preferably chloro or fluoro, and most preferably fluoro.

The aliphatic "alkyl" and "alkenyl" groups may be straight or branched chains having the specified number of carbon atoms, e.g. in the case of $C_1$–$C_6$ alkyl, the alkyl group may have from 1 to 6 carbon atoms.

DETAILED DESCRIPTION

Preferred embodiments of the present invention, including in each case pharmaceutically acceptable salts thereof are:

(2R,3R)-3-[4-(4-cyanophenyl)thiazol-2-yl]-2-(2,4-difluorophenyl)-1-(1H-1,2,4-triazol-1-yl)-2-[[p-(N,N-diethylaminomethyl)benzoyloxy]methoxy]butane (compound of example 1)

(2R,3R)-3-[4-(4-cyanophenyl)thiazol-2-yl]-2-(2,4-difluorophenyl)-1-(1H-1,2,4-triazol-1-yl)-2-[[p-(N,N-di-(2-hydroxyethyl)aminomethyl) benzoyloxy] methoxy]butane (compound of example 2)

(2R,3R)-3-[4-(4-cyanophenyl)thiazol-2-yl]-2-(2,4-difluorophenyl)-1-(1H-1,2,4-triazol-1-yl)-2-[[p-(4-methyl-piperazinyl)methyl]benzoyloxy]methoxy] butane (compound of example 3)

(2R,3R)-3-[4-(4-cyanophenyl)thiazol-2-yl]-2-(2,4-difluorophenyl)-1-(1H-1,2,4-triazol-1-yl)-2-[[p-(N,N-dimethylaminomethyl)benzoyloxy]methoxy]butane (compound of example 4)

(2R,3R)-3-[4-(4-cyanophenyl)thiazol-2-yl]-2-(2,4-difluorophenyl)-1-(1H-1,2,4-triazol-1-yl)-2-[[p-(N-methyl-N-(2-hydroxyethyl)aminomethyl) benzoyloxy] methoxy]butane (compound of example 5)

(2R,3R)-3-[4-(4-cyanophenyl)thiazol-2-yl]-2-(2,4-difluorophenyl)-1-(1H-1,2,4-triazol-1-yl)-2-[[p-(N-ethyl-N-butyl)aminomethyl]benzoyloxy]methoxy] butane (compound of example 6)

(2R,3R)-3-[4-(4-cyanophenyl)thiazol-2-yl]-2-(2,4-difluorophenyl)-1-(1H-1,2,4-triazol-1-yl)-2-[[p-(4-(2-hydroxyethyl)-1-piperazinylmethyl) benzoyloxy] methoxy]butane (compound of example 7)

(2R,3R)-3-[4-(4-cyanophenyl)thiazol-2-yl]-2-(2,4-difluorophenyl)-1-(1H-1,2,4-triazol-1-yl)-2-[[p-[(3RS-hydroxy)-1-piperidinylmethyl]benzoyloxy]methoxy] butane (compound of example 8)

(2R,3R)-3-[4-(4-cyanophenyl)thiazol-2-yl]-2-(2,4-difluorophenyl)-1-(1H-1,2,4-triazol-1-yl)-2-[[p-[(4-(2RS-hydroxyethyl)-1-piperidinylmethyl]benzoyloxy] methoxy]butane (compound of example 9)

(2R,3R)-3-[4-(4-cyanophenyl)thiazol-2-yl]-2-(2,4-difluorophenyl)-1-(1H-1,2,4-triazol-1-yl)2-[[p-[(4-formyl)-1-piperazinylmethyl]benzoyloxy]methoxy] butane (compound of example 10)

(2R,3R)-3-[4-(4-cyanophenyl)thiazol-2-yl]-2-(2,4-difluorophenyl)-1-(1H-1,2,4-triazol-1-yl)-2-[[p-[(4RS-hydroxy)-1-piperidinylmethyl]benzoyloxy]methoxy] butane (compound of example 11)

(2R,3R)-3-[4-(4-cyanophenyl)thiazol-2-yl]-2-(2,4-difluorophenyl)-1-(1H-1,2,4-triazol-1-yl)-2-[[p-[(4-ethyl)-1-piperazinylmethyl]benzoyloxy]methoxy] butane (compound of example 12)

(2R,3R)-3-[4-(4-cyanophenyl)thiazol-2-yl]-2-(2,4-difluorophenyl)-1-(1H-1,2,4-triazol-1-yl)-2-[[p-[(4RS-methyl)-1-piperidinylmethyl]benzoyloxy]methoxy] butane (compound of example 13)

(2R,3R)-3-[4-(4-cyanophenyl)thiazol-2-yl]-2-(2,4-difluorophenyl)-1-(1H-1,2,4-triazol-1-yl)-2-[[p-[(4RS-(N-piperadinyl)-1-piperidinylmethyl]benzoyloxy] methoxy]butane (compound of example 14)

(2R,3R)-3-[4-(4-cyanophenyl)thiazol-2-yl]-2-(2,4-difluorophenyl)-1-(1H-1,2,4-triazol-1-yl)-2-[[p-[(N,N-dipropyl)aminomethyl]benzoyloxy]methoxy]butane (compound of example 15)

(2R,3R)-3-[4-(4-cyanophenyl)thiazol-2-yl]-2-(2,4-difluorophenyl)-1-(1H-1,2,4-triazol-1-yl)-2-[[p-[(3RS-hydroxy)-1-pyrrolidinylmethyl]benzoyloxy]ethoxy] butane (compound of example 16)

(2R,3R)-3-[4-(4-cyanophenyl)thiazol-2-yl]-2-(2,4-difluorophenyl)-1-(1H-1,2,4-triazol-1-yl)-2-[[p-[(N,N-diallyl)aminomethyl]benzoyloxy]methoxy]butane (compound of example 17)

(2R,3R)-3-[4-(4-cyanophenyl)thiazol-2-yl]-2-(2,4-difluorophenyl)-1-(1H-1,2,4-triazol-1-yl)-2-[[p-[(2S,6R-dimethyl-1-piperidinyl)methyl]benzoyloxy] methoxy]butane (compound of example 18)

(2R,3R)-3-[4-(4-cyanophenyl)thiazol-2-yl]-2-(2,4-difluorophenyl)-1-(1H-1,2,4-triazol-1-yl)-2-[[p-[N-ethyl-N-(2-dimethylaminoethyl) aminomethyl] benzoyloxy]methoxy]butane (compound of example 19)

(2R,3R)-3-[4-(4-cyanophenyl)thiazol-2-yl]-2-(2,4-difluorophenyl)-1-(1H-1,2,4-triazol-1-yl)-2-[[p-[(3-thiazolidinyl)methyl]benzoyloxy]methoxy]butane (compound of example 20)

(2R,3R)-3-[4-(4-cyanophenyl)thiazol-2-yl]-2-(2,4-difluorophenyl)-1-(1H-1,2,4-triazol-1-yl)-2-[[p-[(N-methyl-N-(3-dimethylaminopropyl) aminomethyl] benzoyloxy]methoxy]butane (compound of example 21)

(2R,3R)-3-[4-(4-cyanophenyl)thiazol-2-yl]-2-(2,4-difluorophenyl)-1-(1H-1,2,4-triazol-1-yl)-2-[[p-[(3RS-methyl-1-piperidinyl)methyl]benzoyloxy]methoxy] butane (compound of example 22)

(2R,3R)-3-[4-(4-cyanophenyl)thiazol-2-yl]-2-(2,4-difluorophenyl)-1-(1H-1,2,4-triazol-1-yl)-2-[[p-[N-methyl-N-(2-dimethylaminoethyl) aminomethyl] benzoyloxy]methoxy]butane (compound of example 23)

(2R,3R)-3-[4-(4-cyanophenyl)thiazol-2-yl]-2-(2,4-difluorophenyl)-1-(1H-1,2,4-triazol-1-yl)-2-[[p-[N,N- bis-(2RS-hydroxypropyl)aminomethyl]benzoyloxy] methoxy]butane (compound of example 24).

2R,3R)-3-[4-(4-cyanophenyl)thiazol-2-yl]-2-(2,4-difluorophenyl)-1-(1H-1,2,4-triazol-1-yl)-2-[[p-[(1-piperidinyl)methyl]benzoyloxy]methoxy]butane (compound of example 25)

(2R,3R)-3-[4-(4-cyanophenyl)thiazol-2-yl]-2-(2,4-difluorophenyl)-1-(1H-1,2,4-triazol-1-yl)-2-[[p-[(4-morpholinyl)methyl]benzoyloxy]methoxy]butane (compound of example 26)

(2R,3R)-3-[4-(4-cyanophenyl)thiazol-2-yl]-2-(2,4-difluorophenyl)-1-(1H-1,2,4-triazol-1-yl)-2-[[m-[(4-morpholinyl)methyl]benzoyloxy]methoxy]butane (compound of example 27)

(2R,3R)-3-[4-(4-cyanophenyl)thiazol-2-yl]-2-(2,4-difluorophenyl)-1-(1H-1,2,4-triazol-1-yl)-2-[[m-(N,N-diethylaminomethyl)benzoyloxy]methoxy]butane (compound of example 28)

(2R,3R)-3-[4-(4-cyanophenyl)thiazol-2-yl]-2-(2,4-difluorophenyl)-1-(1H-1,2,4-triazol-1-yl)-2-[[m-[N,N-bis(2-hydroxyethyl)aminomethyl]benzoyloxy] methoxy]butane (compound of example 29)

(2R,3R)-3-[4-(4-cyanophenyl)thiazol-2-yl]-2-(2,4-difluorophenyl)-1-(1H-1,2,4-triazol-1-yl)-2-[[m-[(4-methyl-1-piperazinyl)methyl]benzoyloxy]methoxy] butane (compound of example 30)

(2R,3R)-3-[4-(4-cyanophenyl)thiazol-2-yl]-2-(2,4-difluorophenyl)-1-(1H-1,2,4-triazol-1-yl)-2-[[[p-[(4-morpholinyl)methyl]benzoyloxy]methoxy] carbonyloxy]butane (compound of example 31)

(2R,3R)-3-[4-(4-cyanophenyl)thiazol-2-yl]-2-(2,4-difluorophenyl)-1-(1H-1,2,4-triazol-1-yl)-2-[[[p-[N,N-diethylaminomethyl]benzoyloxy]methoxy] carbonyloxy]butane (compound of example 32)

(2R,3R)-3-[4-(4-cyanophenyl)thiazol-2-yl]-2-(2,4-difluorophenyl)-1-(1H-1,2,4-triazol-1-yl)-2-[[[m-[(4-morpholinyl)methyl]benzoyloxy]methoxy] carbonyloxy]butane (compound of example 33)

(2R,3R)-3-[4-(4-cyanophenyl)thiazol-2-yl]-2-(2,4-difluorophenyl)-1-(1H-1,2,4-triazol-1-yl)-2-[[[p-[N,N-bis-(2-hydroxyethyl)aminomethyl]benzoyloxy] methoxy]carbonyloxy]butane (compound of example 34)

(2R,3R)-3-[4-(4-cyanophenyl)thiazol-2-yl]-2-(2,4-difluorophenyl)-1-(1H-1,2,4-triazol-1-yl)-2-[[[p-[(4-methyl-1-piperazinyl)methyl]benzoyloxy]methoxy] carbonyloxy]butane (compound of example 35)

(2R,3R)-3-[4-(4-cyanophenyl)thiazol-2-yl]-2-(2,4-difluorophenyl)-1-(1H-1,2,4-triazol-1-yl)-2-[[[m-[N,N-bis-(2-hydroxyethyl)aminomethyl]benzoyloxy] methoxy]carbonyloxy]butane (compound of example 36)

(2R,3R)-3-[4-(4-cyanophenyl)thiazol-2-yl]-2-(2,4-difluorophenyl)-1-(1H-1,2,4-triazol-1-yl)-2-[[[m-[(4-methyl-1-piperazinyl)methyl]benzoyloxy]methoxy] carbonyloxy]butane (compound of example 37)

(2R,3R)-3-[4-(4-cyanophenyl)thiazol-2-yl]-2-(2,4-difluorophenyl)-1-(1H-1,2,4-triazol-1-yl)-2-[[[m-[N,N-diethylaminomethyl]benzoyloxy]methoxy] carbonyloxy]butane (compound of example 38)

(2R,3R)-3-[4-(4-cyanophenyl)thiazol-2-yl]-2-(2,4-difluorophenyl)-1-(1H-1,2,4-triazol-1-yl)-2-[[[m-[(4-(2'-hydroxyethoxy)ethyl-1-piperazinyl) methyl] benzoyloxy]methoxy]carbonyloxy]butane (compound of example 39)

(2R,3R)-3-[4-(4-cyanophenyl)thiazol-2-yl]-2-(2,4-difluorophenyl)-1-(1H-1,2,4-triazol-1-yl)-2-[[[m-[N-methyl-N-(2-hydroxyethyl)aminomethyl]benzoyloxy] methoxy]carbonyloxy]butane (compound of example 40)

(2R,3R)-3-[4-(4-cyanophenyl)thiazol-2-yl]-2-(2,4-difluorophenyl)-1-(1H-1,2,4-triazol-1-yl)-2-[[[m-[(4'-hydroxy-4-piperidinyl)methyl]benzoyloxy]methoxy] carbonyloxy]butane (compound of example 41)

(2R,3R)-3-[4-(4-cyanophenyl)thiazol-2-yl]-2-(2,4-difluorophenyl)-1-(1H-1,2,4-triazol-1-yl)-2-[[[m-[(4'-carbamyl-4-piperidinyl)methyl]benzoyloxy]methoxy] carbonyloxy]butane (compound of example 42)

(2R,3R)-3-[4-(4-cyanophenyl)thiazol-2-yl]-2-(2,4-difluorophenyl)-1-(1H-1,2,4-triazol-1-yl)-2[[[m-[(4-(2-hydroxyethyl)-1-piperazinyl) methyl]benzoyloxy] methoxy]carbonyloxy]butane (compound of example 43)

The more preferred embodiments of the present invention, including in each case pharmaceutically acceptable salts thereof are:

1,2,4-triazol-1-yl)-2-[[p-[(4-morpholinyl)methyl] benzoyloxy]methoxy]butane (compound of example 26)

1,2,4-triazol-1-yl)-2-[[[p-[N,N-diethylaminomethyl] benzoyloxy]methoxy]carbonyloxy]butane (compound of example 32)

(2R,3R)-3-[4-(4-cyanophenyl)thiazol-2-yl]-2-(2,4-difluorophenyl)-1-(1H-1,2,4-triazol-1-yl)-2-[[[m-[(4-morpholiny)methyl]benzoyloxy]methoxy] carbonyloxy]butane (compound of example 33)

1,2,4-triazol-1-yl)-2-[[[p-[N,N-bis-(2-hydroxyethyl) aminomethyl]benzoyloxy]methoxy]carbonyloxy] butane (compound of example 34)

(2R,3R)-3-[4-(4-cyanophenyl)thiazol-2-yl]-2-(2, 4difluorophenyl)-1-(1H-1,2,4-triazol-1-yl)-2-[[[m-[N, N-b is-(2-hydroxyethyl)aminomethyl]benzoyloxy] methoxy]carbonyloxy]butane (compound of example 36)

1,2,4-triazol-1-yl)-2-[[[m-[N,N-diethylaminomethyl] benzoyloxy]methoxy]carbonyloxy]butane (compound of example 38)

(2R,3R)-3-[4-(4-cyanophenyl)thiazol-2-yl]-2-(2,4-difluorophenyl)-1-(1H-1,2,4-triazol-1-yl)-2-[[[m-[(4-(2'-hydroxyethoxy)ethyl-1-piperazinyl) methyl] benzoyloxy]methoxy]carbonyloxy]butane (compound of example 39)

(2R,3R)-3-[4-(4-cyanophenyl)thiazol-2-yl-2-(2,4-difluorophenyl)-1-(1H-1,2,4-triazol-1-yl)-2-[[[m-[N-methyl-N-(2-hydroxyethyl)aminomethyl]enzoyloxy] methoxy]carbonyloxy]butane (compound of example 40)

(2R,3R)-3-[4-(4-cyanophenyl)thiazol-2-yl]-2-(2,4-difluorophenyl)-1-(1H-1,2,4-triazol-1-yl)-2-[[[m-[(4'-hydroxy-4-piperidinyl)methyl]benzoyloxy]methoxy] carbonyloxy]butane (compound of example 41)

(2R,3R)-3-t4-(4-cyanophenyl)thiazol-2-yl]-2-(2,4-difluorophenyl)-1-(1H-1,2,4-triazol-1-yl)-2-[[[m-[(4'-carbamyl-4-piperidinyl)methyl]benzoyloxy]methoxy]carbonyloxy]butane (compound of example 42)

(2R,3R)-3-[4-(4-cyanophenyl)thiazol-2-yl]-2-(2,4-difluorophenyl)-1-(1H-1,2,4-triazol-1-yl)-2-[[[m-[(4-(2-hydroxyethyl)-1-piperazinyl) methyl]benzoyloxy]methoxy]carbonyloxy]butane (compound of example 43).

The aforementioned preferred embodiments of the present invention are listed in the table below along with their observed molecular ions (M+ or MH+).

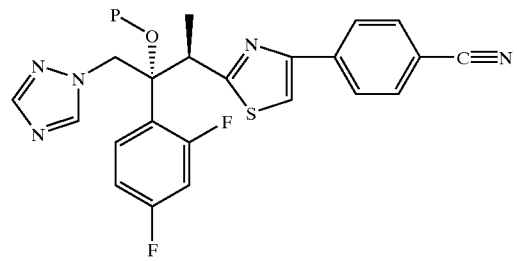

III

| Example | R | Mass Spec |
|---|---|---|
| 1 | | MH+ = 657 |
| 2 | | MH+ = 689 |
| 3 | | MH+ = 684 |
| 4 | | MH+ = 629 |
| 5 | | MH+ = 659 |
| 6 | | MH+ = 685 |
| 7 | | MH+ = 714 |

-continued
| Example | R | Mass Spec |
|---|---|---|
| 8 | 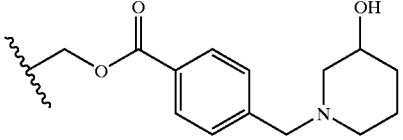 | MH+ = 685 |
| 9 | 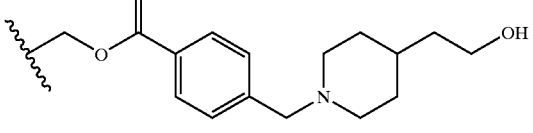 | MH+ = 713 |
| 10 | 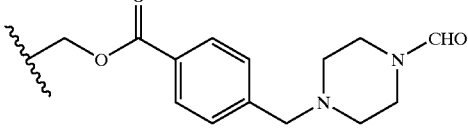 | MH+ = 698 |
| 11 | 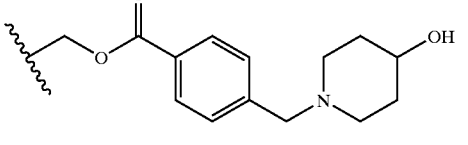 | MH+ = 685 |
| 12 | 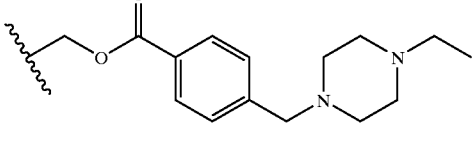 | MH+ = 698 |
| 13 | 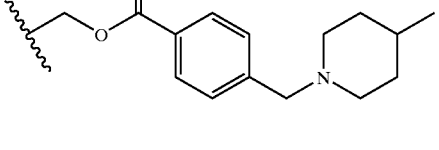 | MH+ = 683 |
| 14 | 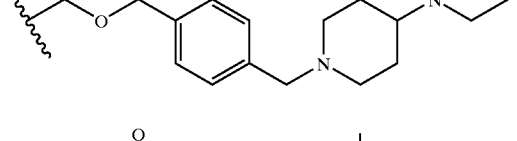 | MH+ = 752 |
| 15 | 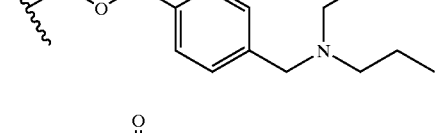 | MH+ = 685 |
| 16 | 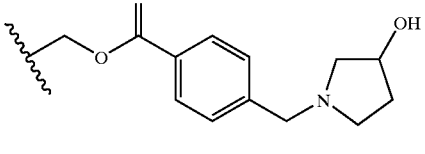 | MH+ = 671 |

-continued
| Example | R | Mass Spec |
|---|---|---|
| 17 | 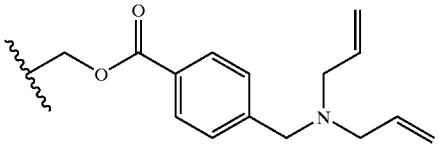 | MH+ = 681 |
| 18 | 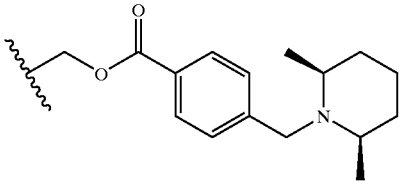 | MH+ = 697 |
| 19 | 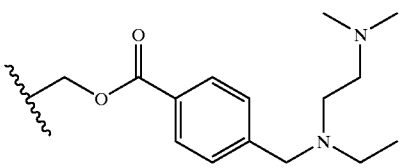 | MH+ = 700 |
| 20 | 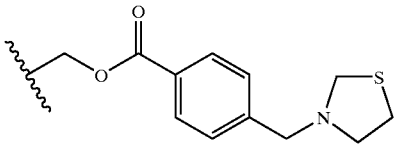 | MH+ = 673 |
| 21 | 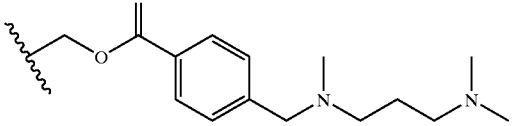 | MH+ = 686 |
| 22 | 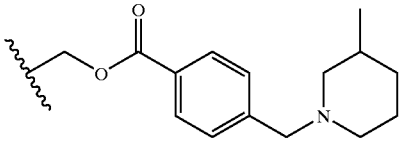 | MH+ = 683 |
| 23 | 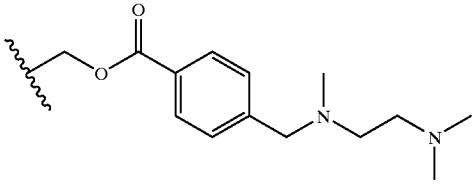 | MH+ = 686 |
| 24 | 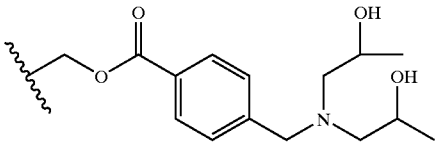 | MH+ = 717 |
| 25 | 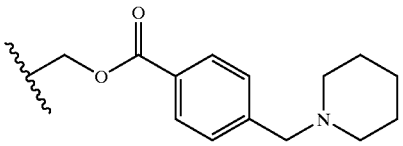 | MH+ = 669 |

-continued
| Example | R | Mass Spec |
|---|---|---|
| 26 | 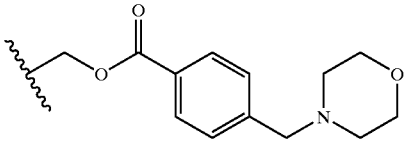 | M+ = 670 |
| 27 | 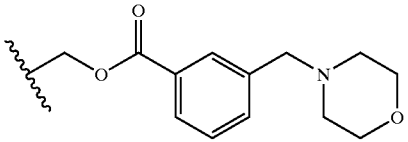 | M+ = 670 |
| 28 | 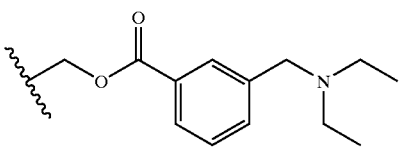 | MH+ = 657 |
| 29 | 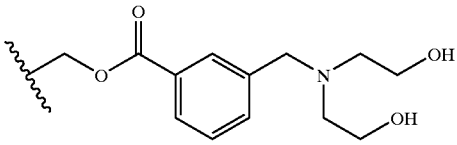 | MH+ = 689 |
| 30 | 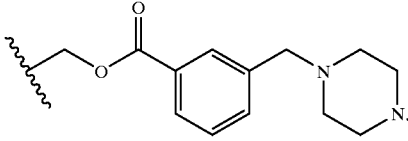 | MH+ = 684 |
| 31 | 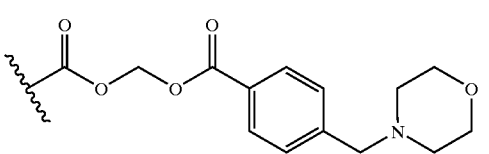 | MH+ = 716 |
| 32 | 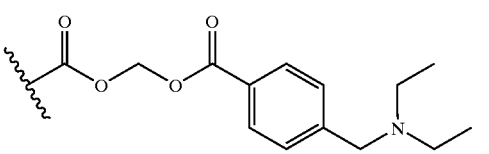 | MH+ = 702 |
| 33 | 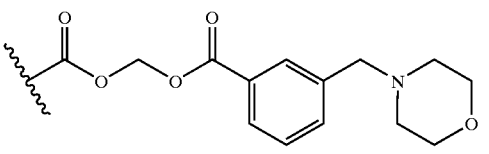 | M+ = 715 |
| 34 | 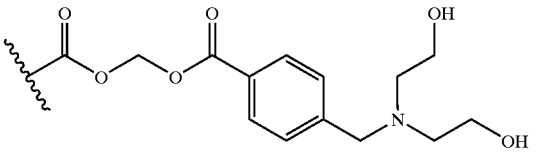 | MH+ = 734 |

-continued
| Example | R | Mass Spec |
|---|---|---|
| 35 | 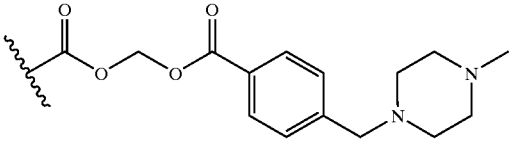 | MH+ = 728 |
| 36 | 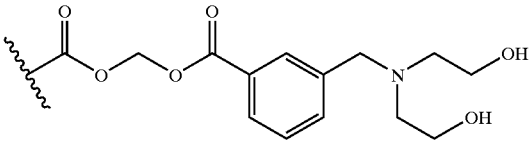 | MH+ = 734 |
| 37 | 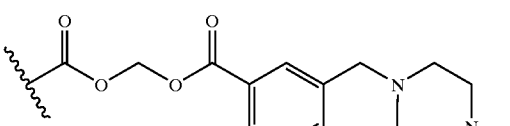 | MH+ = 728 |
| 38 | 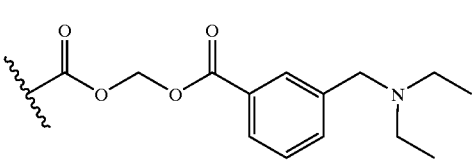 | MH+ = 702 |
| 39 | 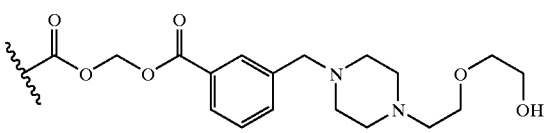 | MH+ = 802 |
| 40 | 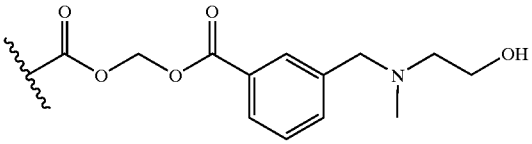 | MH+ = 704 |
| 41 | 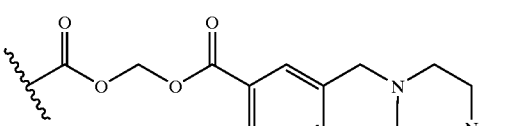 | MH+ = 730 |
| 42 | 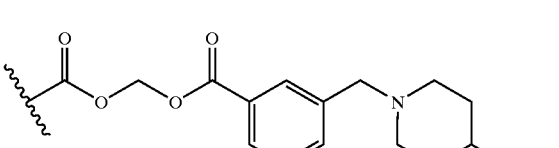 | MH+ = 757 |
| 43 | 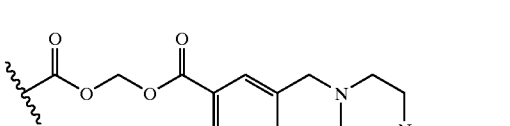 | MH+ = 758 |

The compounds of the present invention can be made by conventional methods. Two suitable procedures are summarized by the following reaction schemes. In both methods, A represents the non-hydroxy portion of a triazole anti-fungal compound of the type containing a tertiary or secondary hydroxy group.

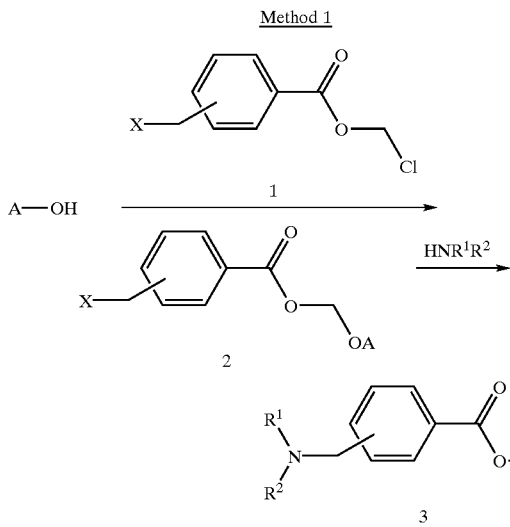

X=Cl, Br or I, preferably Cl

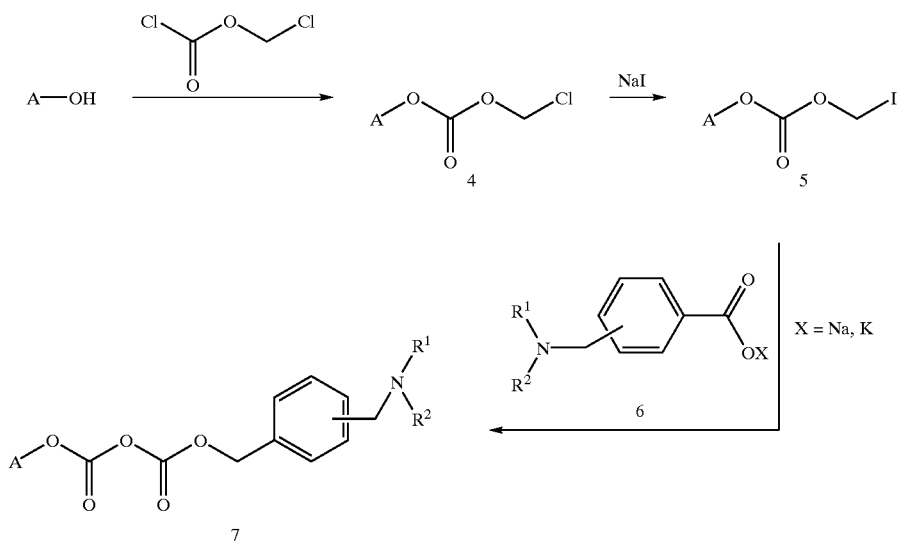

To elaborate on Method 1, the anti-fungal parent compound of interest is converted into ester 2 by reaction with chloride 1 in the presence of a suitable base, such as potassium hydride. The reaction can be carried out in THP or other appropriate solvent and the product is usually purified by column chromatography. Chloride 1 can be prepared by the general method of Iyer et al., Syn. Comm. 25, 2739, 1995 (see Method 1 below in the Illustrative Examples section) or by Method 2 shown below in the Examples). Ester 2 can be subsequently transformed into arylmethylamine 3 by reaction with the desired dialkyl amine in DMF. The reaction occurs between 25° C. and 100° C. and the resulting product can be purified by recrystallization or column chromatography. If an amine salt is used, it will be understood that one molar equivalent of an appropriate base should be added to facilitate the reaction.

The intermediates 2 of the formula

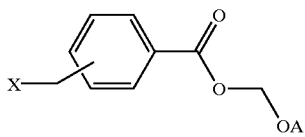

wherein the halomethyl substituent is in the ortho, meta or para position, preferably the meta or para position, X is chloro, bromo or iodo, preferably chloro, and A represents the non-hydroxyl portion of a triazole antifungal compound of the type containing a tertiary or secondary hydroxyl group are another aspect of the present invention. The preferred intermediates are those having the specific "A" groups mentioned above.

The intermediates 2 may be prepared by reacting a suitable halomethyl benzoic acid ester of the formula

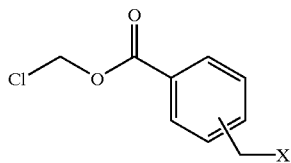

wherein the halomethyl substituent of the phenyl ring is in the ortho, meta or para position, preferably the meta or para position, X is Cl, Br or I, and A represents the non-hydroxyl portion of a triazole antifungal compound of the type containing a tertiary or secondary hydroxyl group with an antifungal agent A—OH wherein A is as defined above in an inert organic solvent such as tetrahydrofuran and in the presence of base such as potassium hydride.

To elaborate on Method 2, the anti-fungal parent compound of interest is transformed into chloromethylformate 4 by reaction with commercially available chloromethylchloroformate (Aldrich Chemical Company) in the presence of an appropriate base in THF or other solvent at 0° C. to 50° C. Appropriate bases include potassium hydride and sodium hydride, among others, with the preferred base being potassium hydride. The product can be purified by column chromatography. Chloromethylformate 4 is converted to iodide 5 by reaction at elevated temperature with NaI in acetone. The crude product from this reaction can be used in the next step, or the product can be purified via column chromatography. In another aspect then, the present invention provides intermediates 4 of the formula

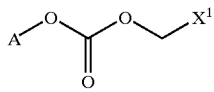

wherein $X^1$ is Cl, Br or I and A is the non-hydroxy portion of a triazole antifungal compound of the type containing a tertiary or secondary hydroxyl group. The preferred intermediates of formula 4 are those having the specific "A" groups mentioned above. Intermediates 4 may be prepared by reacting chloromethylchloroformate with an antifungal agent A—OH in which A is as defined above in an inert organic solvent such as tetrahydrofuran. in the presence of base and, if desired, converting the so-produced chloromethylformate of formula 4 to the corresponding compound of formula 4 wherein $X^1$ is Br or I by reaction with an alkali metal bromide or iodide. Iodide 5 is converted to the final product 7 by reaction with carboxylate salt 6 in acetonitrile or other appropriate organic solvent. The efficiency of the reaction can be increased by adding small amounts of 18-crown-6 or other appropriate crown ether. Carboxylate salt 6 can be prepared by the method disclosed in Lombardino et al in U.S. Pat. No. 4,623,486. The product can be purified by recrystallization or column chromatography. If an amine salt is used, it will be understood that one molar equivalent of an appropriate base should be added to facilitate the reaction. It is also possible to directly convert chloride 4 to the final product by reaction with carboxylate salt 6 at elevated temperatures.

It will be understood that where the substituent groups used in the above reactions contain certain reaction-sensitive functional groups such as amino or carboxylate groups which might result in undesirable side-reactions, such groups may be protected by conventional protecting groups known to those skilled in the art. Suitable protecting groups and methods for their removal are illustrated, for example, in *Protective Groups in Organic Synthesis*, Theodora W. Greene (John Wiley & Sons, 1991). It is intended that such "protected" intermediates and end-products are included within the scope of the present disclosure and claims.

The desired end-product of formula I may be recovered in the form of a pharmaceutically acceptable acid addition salt, e.g. by addition of the appropriate acid such as HCl, HI or methane-sulfonic acid to the amine.

It will be appreciated that certain products within the scope of formula I may have substituent groups which can result in formation of optical isomers. It is intended that the present invention include within its scope all such optical isomers as well as epimeric mixtures thereof, i.e. R- or S- or racemic forms.

The pharmaceutically active compounds of this invention may be used alone or formulated as pharmaceutical compositions comprising, in addition to the active triazole ingredient, a pharmaceutically acceptable carrier, adjuvant or diluent. The compounds may be administered by a variety of means, for example, orally, topically or parenterally (intravenous or intramuscular injection). The pharmaceutical compositions may be in solid form such as capsules, tablets, powders, etc. or in liquid form such as solutions, suspensions or emulsions. Compositions for injection may be prepared in unit dose form in ampules or in multidose containers and may contain additives such as suspending, stabilizing and dispersing agents. The compositions may be in ready-to-use form or in powder form for reconstitution at the time of delivery with a suitable vehicle such as sterile water.

Alternatively, the compounds of the present invention can be administered in the form of a suppository or pessary, or they may be applied topically in the form of a lotion, solution, or cream. Additionally, they may be incorporated (at a concentration up to 10%) into an ointment consisting of a white wax or soft, white paraffin base together with the required stabilizers and/or preservatives.

The compounds of the invention are useful because they possess pharmacological activities in animals, including particularly mammals and most particularly, humans. Specifically, the compounds of the present invention are useful for the treatment or prevention of topical fungal infections, including those caused by species of Candida, Trichophyton, Microsporum, or Epidermophyton. Additionally, they are useful for the treatment of mucosal infections caused by *Candida albicans*. They can also be used in the treatment of systemic fungal infections caused, for example, by species of *Candida albicans, Cryptococcus neoformans, Aspergillus flavus, Aspergillus fumigatus*, Coccidioides, Paracoccidiodes, Histoplasma, or Blastomyces.

Thus, according to another aspect of the invention, there is provided a method of treating a fungal infection which comprises administering a therapeutically effective amount of the compound to a host, particularly a mammalian host and most particularly a human patient. The use of the compounds of the present invention as pharmaceuticals and the use of the compounds of the invention in the manufacture of a medicament for the treatment of fungal infections are also provided.

The dosage to be administered depends, to a large extent, on the particular compound being used, the particular composition formulated, the route of administration, the nature and condition of the host and the particular situs and organism being treated. Selection of the particular preferred dosage and route of application, then, is left to the discretion of the physician or veterinarian. In general, however, the compounds may be administered parenterally or orally to mammalian hosts in an amount of from about 5 mg/day to about 1.0 g/day. These doses are exemplary of the average case, and there can be individual instances where higher or lower dosages are merited, and such dosages are within the scope of this invention. Furthermore, administration of the compounds of the present inventions can be conducted in either single or divided doses.

The in vitro evaluation of the antifungal activities of the compounds of the invention can be performed by determining the minimum inhibitory concentration (MIC). The MIC is the concentration of test compound which inhibits the growth of the test microorganism. In practice, a series of agar plates, each having the test compound incorporated at a specific concentration, is inoculated with a fungal strain and each plate is then incubated for 48 h at 37° C. The plates are examined for the presence or absence of fungal growth, and the relevant concentration is noted. Microorganisms which can be used in the test include *Candida albicans, Asperigillus fumigatus*, Trichophyton spp., Microsporum spp., *Epidermophyton floccosum, Coccidioides immitis*, and *Torulopsos galbrata*. It should be recognized that, as prodrugs, some compounds of the invention may not be active in the in vitro test.

The in vivo evaluation of compounds of the present invention can be carried out at a series of dose levels by intraperitoneal or intravenous injection or by oral administration to mice which have been inoculated with a strain of fungus (e.g. *Candida albicans*). Activity is determined by comparing the survival of the treated group of mice at different dosage levels after the death of an untreated group of mice. The dose level at which the test compound provides 50% protection against the lethal effect of the infection is noted.

The compounds of the present invention substantially increase the solubility of the parent triazole antifungal compound and also release the bioactive parent compound (i.e. function as a prodrug) in both rat and human plasma. As shown in the table below, this is not the case with the triazole derivatives of WO 97/28169.

| Compound | Solubility (mg/mL) | Release of Parent in Human Plasma |
| --- | --- | --- |
| Parent | <0.006 | — |
| Compound of Example 1 | >1 | Yes |
| Example 7 of WO 97/28169 | >1 | No |

ILLUSTRATIVE EXAMPLES

The following examples illustrate the invention, but are not intended as a limitation thereof. The abbreviations used in the examples are conventional abbreviations well-known to those skilled in the art. Some of the abbreviations used are as follows:

| | |
| --- | --- |
| h = | hour(s) |
| rt = | room temperature |
| mol = | mole(s) |
| mmol = | mmole(s) |
| g = | gram(s) |
| THF = | tetrahydrofuran |
| L = | liter(s) |
| mL = | milliliter(s) |
| $Et_2O$ = | diethyl ether |
| EtOAc = | ethyl acetate |
| MeOH = | methanol |
| DMF = | dimethylformamide |
| DABCO = | 1,4-Diazabicyclo[2.2.]octane |

In the following examples, all temperatures are given in degrees Centigrade. Melting points were determined on an electrothermal apparatus and are not corrected. Proton nuclear magnetic resonance ($^1H$ NMR) spectra were recorded on a Bruker AM-300 or a Varian Gemini 300 spectrometer. All spectra were determined in $CDCl_3$, DMSO-$d_6$, $CD_3OD$, or $D_2O$ unless otherwise indicated. Chemical shifts are reported in δ units relative to tetramethylsilane (TMS) or a reference solvent peak and interproton coupling constants are reported in Hertz (Hz). Splitting patterns are designated as follows: s, singlet; d, doublet; t, triplet; q, quartet; m, multiplet; br, broad peak; dd, doublet of doublets; dt, doublet of triplets; and app d, apparent doublet, etc. Mass spectra were recorded on a Kratos MS-50 or a Finnegan 4500 instrument utilizing direct chemical ionization (DCI, isobutene), fast atom bombardment (FAB), or electron ion spray (ESI).

Analytical thin-layer chromatography (TLC) was carried out on precoated silica gel plates (60F-254) and visualized using UV light, iodine vapors, and/or staining by heating with methanolic phosphomolybdic acid. Column chromatography, also referred to as flash chromatography, was performed in a glass column using finely divided silica gel at pressures somewhat above atmospheric pressure.

Preparation of (3-Chloromethyl)Benzoic Acid Chloromethyl Ester

A. Method 1

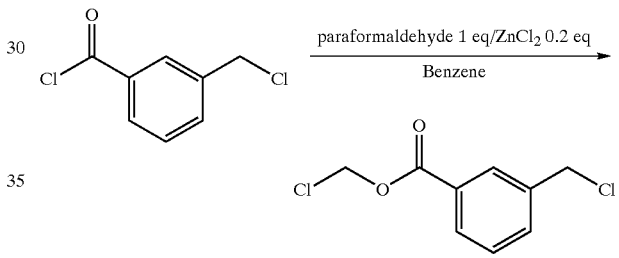

To a cooled (0° C.) mixture of paraformaldehyde (0.79 g, 26.4 mmol) and zinc chloride (72 mg, 0.53 mmol) in benzene (10 mL) was added dropwise the acid chloride (5.0 g, 26.4 mmol) over a period of 15 minutes. The mixture was then heated at 55° C. overnight. The mixture was then filtered and the filtrate concentrated. Purification of the crude product via flash chromatography (100% Hexanes) yielded 2.7 g of the title compound as a colorless oil.

B. Method 2

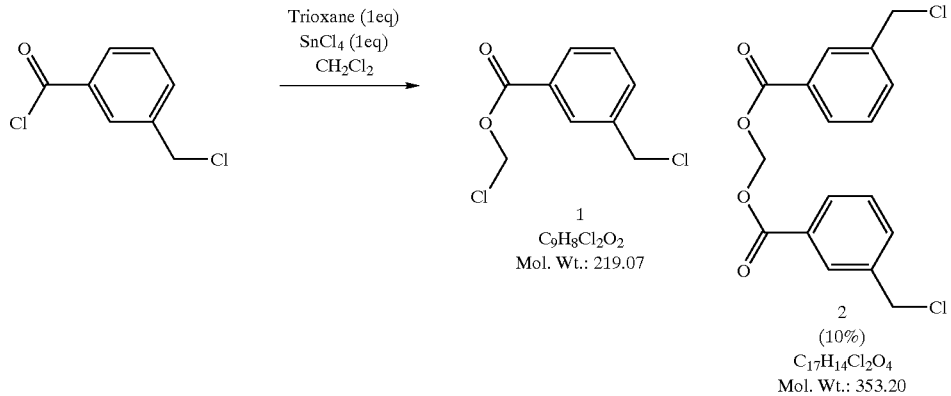

MATERIALS:
 3-Chloromethylbenzoyl chloride: 30 g (0.159 mole, 22.6 mL, Aldrich)
 Tin (IV) Chloride: (41.35 g, 18.57 mL, 158 mole, Aldrich)
 1,3,5-trioxane (14.29 g of 99% purity, 0.158 mole, Aldrich)
 Dichloromethane (120 mL, EM Science, HPLC grade, KF=0.2 mG/mL)
 Heptane (470 mL, EM Science, HPLC grade)
 Ethylacetate (4.5 mL, EM Science, HPLC grade)
 Aq. $NaHCO_3$ solution (saturated); 100 ml
 Water (Deionised, 220 mL)

PROCEDURE:

A 500 ml three neck round bottom flash equipped with a nitrogen inlet, reflux condenser, addition funnel, mechanical stirrer and immersion thermometer was charged with 60 mL $CH_2Cl_2$ (KF=0.2 mg/mL) and 3-chloromethylbenzoylchloride. Tin (IV) chloride was added via the addition funnel with stirring over a period of 2 minutes maintaining a temperature of 20° C.–22° C. 1,3,5-trioxane was added to the stirred mixture. The majority of the 1,3,5-trioxane remains undissolved.

The stirred suspension was kept at 20° C.–22° C. for 24 hours at the end of which the conversion was 99% (L.C. area percent). Approximately 10% of the dimer (2) was also observed by HPLC.

The reaction mixture was quenched by the addition of 120 mL water via the addition funnel maintaining the internal temperature between 15° C.–20° C.

The reaction mixture (containing some suspended solid particles) was filtered through a sintered glass funnel (polish filtration) and the solids were washed with 120 mL $CH_2Cl_2$. After settling, the two layers clearly separated.

The lower $CH_2Cl_2$ layer containing the product was separated from the top aqueous layer. The organic layer was washed with 100 mL water and the lower $CH_2Cl_2$ layer containing the product was separated from the top aqueous layer.

The lower $CH_2Cl_2$ layer containing the product was separated from the top aqueous layer. The organic layer was washed with 100 mL saturated aq. $NaHCO_3$ solution and the lower $CH_2Cl_2$ layer containing the product was separated from the top aqueous layer.

The lower $CH_2Cl_2$ layer containing the product was separated from the top aqueous layer. The $CH_2Cl_2$ was then replaced by heptane via distillation (under atmospheric pressure) maintaining a total volume of approximately 450 mL.

1. Distillation was discontinued when the batch temperature reached approximately 80° C. NMR analysis of the mixture indicated complete removal of $CH_2Cl_2$ at this point.
2. Approximately 470 mL heptane was used.

The mixture was cooled down to 22° C. Ethylacetate (4.5 mL) was added to the stirred mixture and the stirred mixture was kept at 22° C. for 18 h.

1. The less soluble methanediol bis [3-chloromethyl) benzoate] (2) is crystallized out in this process. Addition of ethylacetate helps to keep the desired product (1) in solution.
2. When the heptane solution is cooled down to approximately 30–40° C., some crystallization of the dimer was observed and a seed bed is formed.
3. If the dimer does not crystallize by cooling down to 22° C., additional cooling to 0–5° C. may be necessary for the seed bed to be formed.

The crystals (dimer 2) were filtered and washed with 60 mL heptane.

1. Approximately 4.4 gm of the dimer, methanediol bis[3-chloromethyl)benzoate] was obtained.

The combined filtrate and wash containing the product was concentrated via distillation under house vacuum to approximately 100 mL volume. The mixture was cooled to 22° C. over a period of one hour with seeding (at 35° C.).

1. Crystallization begins at approximately 30° C. to 35° C.
2. Since the compound melts at 42° C., the mixture should not be seeded above 40° C.

The stirred mixture was cooled to 0–5° C. over a period of 30 minutes and then kept at 0–5° C. for 2 hours. The crystals were filtered, washed with 20 mL of cold (10° C.) heptane, and dried in a vacuum oven at 20–22° C. with a flow of nitrogen for 18 hours to yield 25.8 g (74% yield).

ANALYSES:
M.P.=41–42° C.
NMR=consistent with the structure.
HPLC
 Instrument: Shimadzu LC-10AS
 HPLC Detector: Shimadzu SPD M10A Diode Array (260 nm)
 Column: YMC ODS AQ 4.6×150 mm, S-3 μm, 120A
 Injection vol: 10 μL
 Flow Rate: 1.5 mL/min
 Run Time: 25 min
 Eluent A: $CH_3CN$/water 10:90
 Eluent B: $CH_3CN$/water 90:10

| Gradient Table: | Time (minutes) | % Eluent A | % Eluent B |
|---|---|---|---|
| (linear gradient) | 0 | 60 | 40 |
|  | 5 | 60 | 40 |
|  | 15 | 0 | 100 |
|  | 20 | 0 | 100 |
|  | 23 | 60 | 40 |
|  | 25 | stop |  |

Retention Times:
 3-Chloromethylbenzoyl chloride 12.28 min.
 3-Chloromethylbenzoic acid (formed by hydrolysis of the acid chloride) 3.46 min.
 (3-Chloromethyl)benzoic acid chloromethyl ester 11.67 min.
 Methanediol bis [3-chloromethyl)benzoate] (2) 14.67 min.

A. (2R,3R)-3-[4-(4-Cyanophenyl)thiazol-2-yl]-2-(2, 4-difluorophenyl)-1-(1H-1,2,4-triazol-1-yl)-2-[[m-(N,N-diethylaminomethyl)benzoyloxy]methoxy] butane (Compound of Example 28)

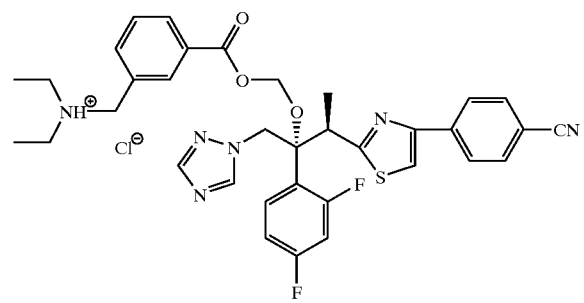

This two step general procedure can be employed for the preparation of compounds of examples 1 to 30.

(2R,3R)-3-[4-(4-Cyanophenyl)thiazol-2-yl]-2-(2,4-difluorophenyl)-1-(1H-1,2,4-triazol-1-yl)-2-[[(m-chloromethyl)benzoyloxy]methoxy]butane

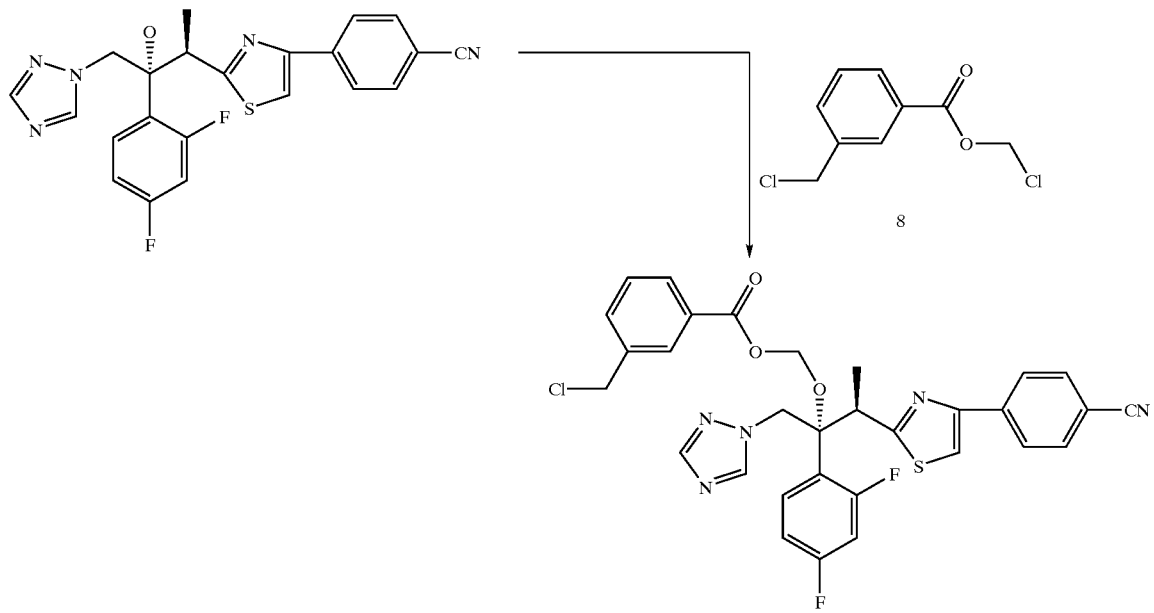

(2R,3R)-3-[4-(4-cyanophenyl)thiazol-2-yl]-2-(2,4-difluorophenyl)-1-(1H-1,2,4-triazol-1-yl)butan-2-ol (1.09 mmol) was added to a suspension of potassium hydride (1.31 mmol) in THF at 0° C. The heterogeneous mixture was stirred for 0.25 hours and chloride 8 (1.14 mmol, prepared via the method of Iyer et al, Syn. Comm. 25, 2739, 1995) was added. The reaction was allowed to stir at 0° C. for 2 hours, and then was allowed to warm to room temperature and stirred for 7 hours. The excess base was carefully quenched with water, and the crude reaction was extracted into ethyl acetate. The layers were separated and the organic layer was washed with water, brine, and was dried over $Na_2SO_4$. Purification of the crude product via column chromatography yielded 300 mg of the subtitled compound as a colorless oil. $^1H$ NMR ($CDCl_3$) δ 8.11 (s, 1H), 7.94 (d, 2H, J=8.5), 7.88 (s, 1H), 7.79 (d, 1H, J=7.8), 7.70 (m, 3H), 7.56 (d, 1H, J=7.8), 7.42 (m, 2H), 7.29 (m, 1H), 6.85 (m, 2H), 6.20 (s, 2H), 5.35 (d, 2H, J=18), 5.03 (d, 2H, J=18), 4.14 (m, 1H), and 1.29 (m, 3H). MS (M+=619).

(2R,3R)-3-[4-(Cyanophenyl)thiazol-2-yl]-2-(2,4-difluorophenyl)-1-(1H-1,2,4-triazol-1-yl)-2-[[(m-N-N-diethylaminomethyl)benzoyloxy]methoxy]butane Hydrogen Chloride

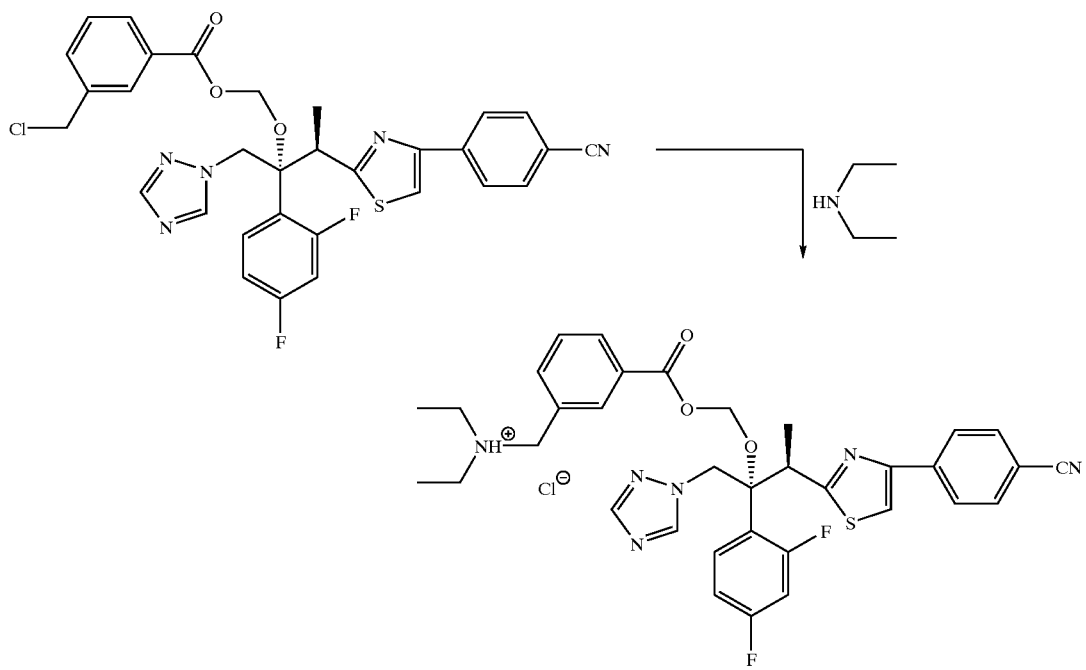

N-N-diethyl amine (1.66 mmol) was added to a solution of (2R,3R)-3-[4-(4-cyanophenyl)thiazol-2-yl]-2-(2,4-difluorophenyl)-1-(1H-1,2,4-triazol-1-yl)-2-[[(m-chloromethyl)benzoyloxy]methoxy]butane (0.33 mmol) in DMF (5 mL). The solution was heated to 40° C. for 3 hours, was cooled to room temperature, and the DMF and excess diethyl amine were removed at reduced pressure. Et$_2$O was added (2 mL), followed by 2 mL of a 1M solution of HCl in Et$_2$O, and the resulting solution was allowed to stir at room temperature overnight. The crude reaction was evaporated to dryness, and the resulting light yellow solid was dissolved in H$_2$O (ca 30 mL) and lyophilized, resulting in 223 mg of the subtitled compound as a yellow solid. $^1$H NMR (DMSO) δ 11.06 (br s, 1H), 9.00 (br s, 1H), 8.66 (br s, 1H), 8.23 (s, 1H), 8.06 (m, 2H), 7.96 (m, 2H), 7.87 (d, 2H, J=8), 7.82 (m, 1H), 7.47 (m, 1H), 7.37 (m, 1H), 7.22 (m, 1H), 7.02 (m, 1H), 6.04 (s, 2H), 5.39 (d, 1H, J=16), 5.21 (d, 1H, J=16), 4.46 (m, 4H), 4.30 (m, 2H), 4.07 (m, 1H), and 1.21 (m, 9H). MS (M+= 619).

B. (2R,3R)-3-[4-(4-Cyanophenyl)thiazol-2-yl]-2-(2,4-difluorophenyl)-1-(1H-1,2,4-triazol-1-yl)-2-[[[p-[(4-morpholinyl)methyl]benzoyloxy]ethoxy]carbonyloxy]butane (Compound of Example 31)

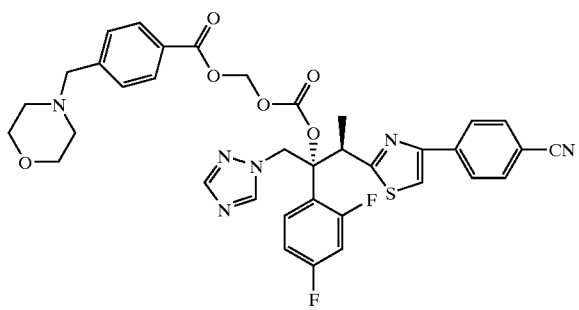

This three step general procedure can be employed for the preparation of compounds of example 31 to 43.

(2R,3R)-3-[4-(4-Cyanophenyl)thiazol-2-yl]-2-(2,4-difluorophenyl)-1-(1H-1,2,4-triazol-1-yl)-2-[[chloromethoxy]carbonyloxy]butane

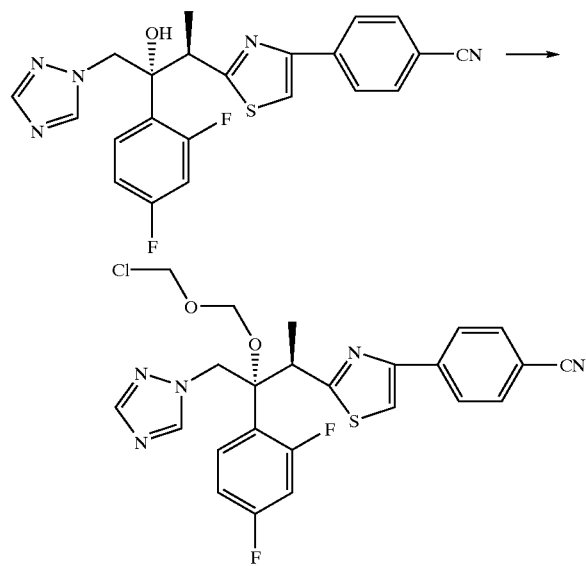

(2R,3R)-3-[4-(4-Cyanophenyl)thiazol-2-yl]-2-(2,4-difluorophenyl)-1-(1H-1,2,4-triazol-1-yl)butan-2-ol (5.8 mmol) was added to a suspension of potassium hydride (7 mmol) in THF at 0° C. and was allowed to stir for 0.5 hours. Choromethyl chloroformate (5.8 mmol, in 2 mL THF) was added dropwise and the reaction was allowed to warm to room temperature and stirred for 4 hours. The crude reaction was diluted with EtOAc, and was sequentially washed with H$_2$O, 0.1N HCl, H$_2$O, and brine. The organic layer was dried over MgSO$_4$ and was concentrated to afford 3.43 g of the subtitled product as a pale yellow solid. 1H NMR (DMSO) δ 8.47 (s, 1H), 8.29 (s, 1H), 8.08 (s, 1H), 7.97 (d, 2H, J=8), 7.88 (d, 2H, J=8), 7.26–7.12 (m, 3H), 5.93 (d, 1H, J=6), 5.90 (d, 1H), J=6), 5.70 (d, J=1H, J=15), 5.36 (d, 1H, J=15), 4.02 (q, 1H, J=7), and 1.48 (d, 3H, J=7); MS (MH+=530).

(2R,3R)-3-[4-(4-Cyanophenyl)thiazol-2-yl]-2-(2,4-difluorophenyl)-1-(1H-1,2,4-triazol-1-yl)-2-[[iodomethoxy]carbonyloxybutane

NaI (19.4 mmol) was added to an acetone solution of (2R,3R)-3-[4-(4-cyanophenyl)thiazol-2-yl]-2-(2,4-difluorophenyl)-1-(1H-1,2,4-triazol-1-yl)-2-[[chloromethoxy]carbonyloxy]butane (6.5 mmol). The reaction was heated to 50° C. for 5 hours. After cooling to room temperature, the crude reaction was filtered, concentrated, and then dissolved in EtOAc. The organic layer was washed sequentially with aqueous solutions of NaHCO$_3$ and Na$_2$S$_2$O$_3$. The organic layer was then washed with H$_2$O, dried over MgSO$_4$, and was concentrated to obtain 3.76 g of the subtitled compound as a yellow solid. $^1$H NMR (DMSO) δ 8.47 (s, 1H), 8.29 (s, 1H), 8.08 (s, 1H), 7.97 (d, 2H, J=8), 7.88 (d, 2H, J=8), 7.26–7.12 (m, 3H), 6.08 (s, 2H), 5.70 (d, J=1H, J=15), 5.36 (d, 1H), J=15), 4.02 (q, 1H, J=7), and 1.48 (d, 3H, J=7); MS (MH+=622).

(2R,3R)-3-[4-(4-Cyanophenyl)thiazol-2-yl]-2-(2,4-difluorophenyl)-1-(1H-1,2,4-triazol-1-yl)-2-[[[p-[(4-morpholiny)methyl]benzoyloxy]methoxy]carbonyloxy]butane (Compound of Example 31)

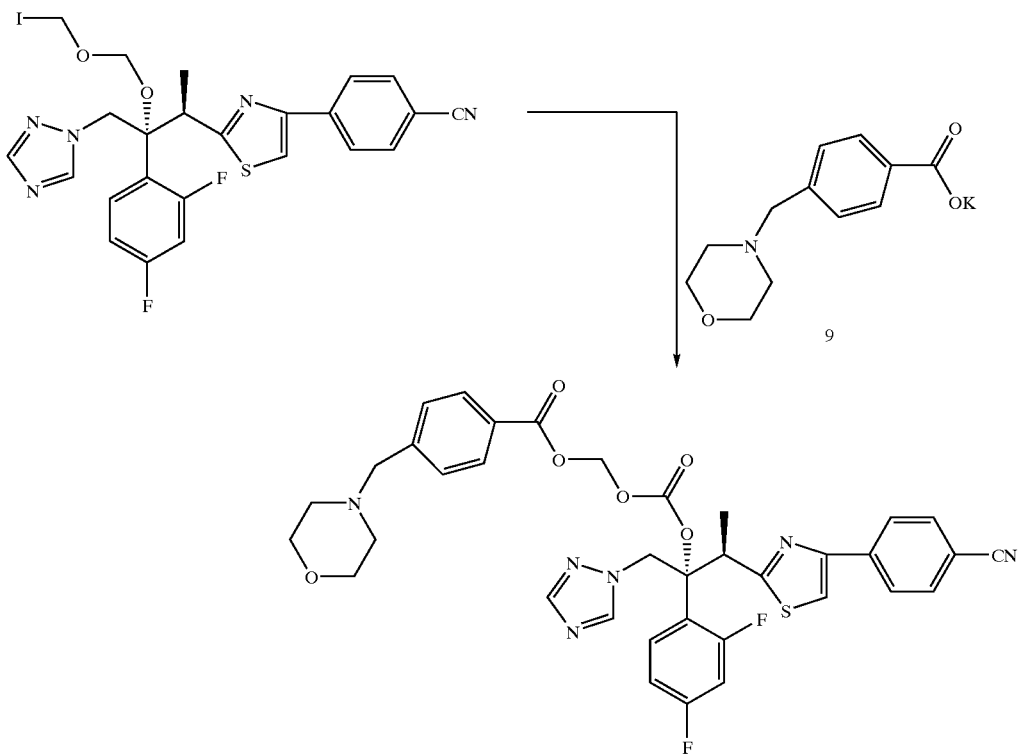

(2R,3R)-3-[4-(4-cyanophenyl)thiazol-2-yl]-2-(2,4-difluorophenyl)-1-(1H-1,2,4-triazol-1-yl)-2-[[iodomethoxy]carbonyloxy]butane (1 mmol) was added to an acetonitrile solution of the carboxylate salt 9 (1.6 mmol, prepared by the method of Lombardino et al, U.S. Pat. No. 4,623,486) and 18-crown-6 (1.6 mmol), and the reaction was allowed to stir for 4 hours. The solution was concentrated at reduced pressure, and was purified via column chromatography on silica. 0.48 g of the subtitled compound was obtained as a white solid. $^1$H NMR (DMSO) δ 8.44 (s, 1H), 8.21 (s, 1H), 7.92 (d, 2H, J=8), 7.91 (d, 2H, J=8), 7.84 (s, 1H), 7.81 (d, 2H, J=8), 7.47 (d, 2H, J=8), 7.20–7.02 (m, 3H), 5.95 (d, 1H, J=6), 5.93 (d, 1H, J=6), 5.66 (d, 1H, J=15), 5.35 (d, 1H, J=15), 4.01 (q, 1H, J=7), 3.56 (br, s, 4H), 3.53 (s, 2H), 2.34 (br s, 4H), and 1.45 (d, 3H, J=7). MS (MH+=716).

We claim:

1. A compound of the formula

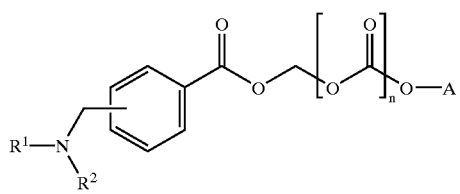

I wherein A is the non-hydroxy portion of a triazole antifungal compound of the type containing a secondary or tertiary hydroxy group, n is 0 or 1, and $R^1$ and $R^2$ are hydrogen, $C_1$–$C_6$ alkyl or $C_2$–$C_6$ alkenyl, said alkyl or alkenyl group being optionally substituted by a hydroxy or dimethylamino group, or a pharmaceutically acceptable salt thereof.

2. A compound of claim 1 wherein A represents the non-hydroxy portion of a triazole antifungal compound of the type containing a tertiary hydroxy group.

3. A compound of claim 2 wherein A is a group of the formula

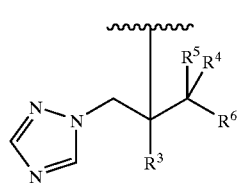

II wherein $R^3$ represents a phenyl group substituted by one or more halogen atoms;

$R^4$ represents hydrogen or $CH_3$;

$R^5$ represents hydrogen, or taken together with $R^4$ may represent $=CH_2$;

$R^6$ represents a 5- or 6-membered nitrogen-containing ring which may be optionally substituted by one or more groups selected from halogen, =O, phenyl substituted by one or more groups selected from CN, $(C_6H_4)$—$OCH_2CF_2CHF_2$ and CH=CH—$(C_6H_4)$—$OCH_2CF_2CHF_2$, or phenyl subsituted by one or more groups selected from halogen and methylpyrazolyl.

4. A compound as claimed in claim 3 wherein $R^3$ is 2,4-difluorophenyl.

5. A compound as claimed in claim 4 wherein $R^4$ is methyl and $R^5$ is hydrogen.

6. A compound as claimed in claim 5 wherein $R^6$ is 4-(4-cyanophenyl)thiazol-2-yl.

7. A compound of claim 6 wherein n is 0 or 1; $R^1$ and $R^2$ are $C_1$–$C_6$ alkyl or $C_2$–$C_6$ alkenyl, said alkyl or alkenyl group being optionally substituted by a hydroxy or dimethylamino group, or a pharmaceutically acceptable salt thereof.

8. A compound selected from:
- (2R,3R)-3-[4-(4-cyanophenyl)thiazol-2-yl]-2-(2,4-difluorophenyl)-1-(1H-1,2,4-triazol-1-yl)-2-[[p-N,N-diethylaminomethyl)benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[p-(N,N,-di-(2-hydroxyethyl)aminomethyl)benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[p-(N,N-dimethylaminomethyl)benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-[[p-N-methyl-N-(2-hydroxyethyl)aminomethyl)benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[p-(N-ethyl-N-butyl)aminomethyl]benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[p-[(N,N-dipropyl)aminomethyl]benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[p-[(N,N-diallyl)aminomethyl]benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[p-[N-ethyl-N-(2-dimethylaminoethyl)aminomethyl]benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[p-[(N-methyl-N-(3-dimethylaminopropyl)aminomethyl]benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[p-[(N-methyl-N-(2-dimethylaminoethyl)aminomethyl]benzoyloxy]methoxy]butane, or a pharmaceutically acceptable salt thereof
- (2R,3R)-3-(4-(4-cyanophenyl)thiazol-2-yl]-2-(2,4-difluorophenyl)-1-(1H-1,2,4-triazol-1-yl)-2-[[p-[N-bis-(2RS-hydroxypropyl)aminomethyl]benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[m-(N,N-diethylaminomethyl)benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[m-[N,N-bis(2-hydroxyethyl)aminomethyl]benzoyloxy]methoxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[[p-[N,N-diethylaminomethyl]benzoyloxy) methoxy] carbonyloxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[[p-[N,N-bis-(2-hydroxyethyl)aminomethyl]benzoyloxy]methoxy]carbonyloxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[[m-[N,N-bis-(2-hydroxyethyl)aminomethyl]benzoyloxy]methoxy]carbonyloxy]butane, or a pharmaceutically acceptable salt thereof
- (2R,3R)-3-[4-(4-cyanophenyl)thiazol-2-yl]-2-(2,4-difluorophenyl)-1-(1H-1,2,4,-triazol-1-yl)-2-[[[m-[N,N-diethylaminomethyl]benzoyloxy]methoxy]carbonyloxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[[m-[N-methyl-N-(2-hydroxyethyl)aminomethyl]benzoyloxy]methoxy]carbonyloxy]butane, or a pharmaceutically acceptable salt thereof.

9. A compound selected from:
- (2R,3R)-3-[4-(4-cyanophenyl)thiazol-2-yl]-2-(2,4-difluorophenyl)-1-(1H-1,2,4-triazol-1-yl)-2-[[[p-[N,N-diethylaminomethyl]benzoyloxy]methoxy]carbonyloxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[[p-[N,N-bis-(2-hydroxyethyl)aminomethyl]benzoyloxy]methoxy]carbonyloxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[[m-[N,N-bis-(2-hydroxyethyl)aminomethyl]benzoyloxy]methoxy]carbonyloxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[[m-[N,N-diethylaminomethyl]benzoyloxy]methoxy]carbonyloxy]butane, or a pharmaceutically acceptable salt thereof
- (2R,3R)-3-[4-(4-cyanophenyl)thiazol-2-yl]-2-(2,4-difluorophenyl)-1-(1H-1,2,4-triazol-1-yl)-2-[[[m-[N-methyl-N-(2-hydroxyethyl)aminomethyl]benzoyloxy]methoxy]carbonyloxy]butane, or a pharmaceutically acceptable salt thereof.

10. A compound of claim 1 where A is

-continued

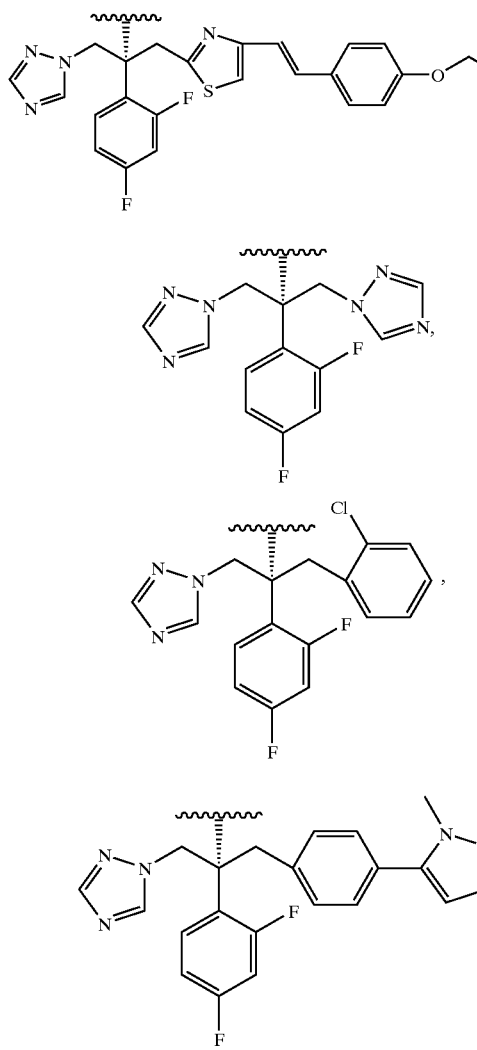

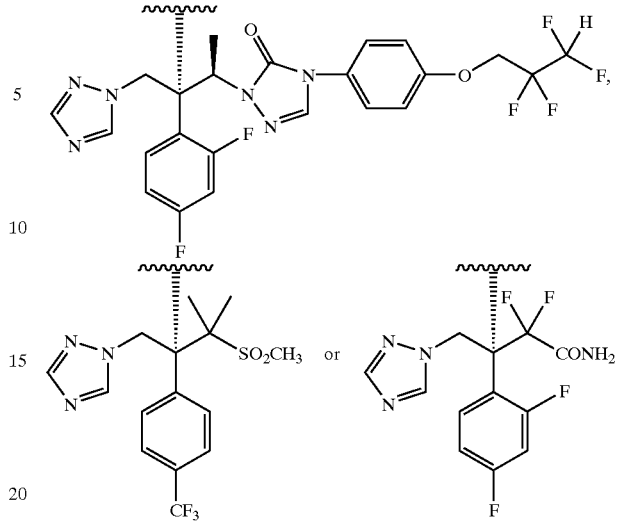

11. A compound of the formula

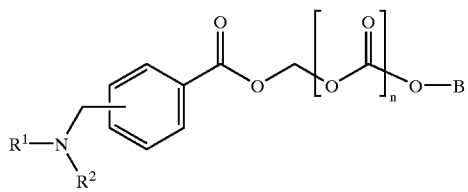

IA wherein B is the non-hydroxy portion of a triazole antifungal compound of the type containing a secondary hydroxy group, n is 0 or 1, and $R^1$ and $R^2$ are hydrogen, $C_1$–C6 alkyl or $C_2$–$C_6$ alkenyl, said alkyl or alkenyl group being optionally substituted by a hydroxy or dimethylamino group, or a pharmaceutically acceptable salt thereof.

12. A compound of claim 11 wherein B is either:

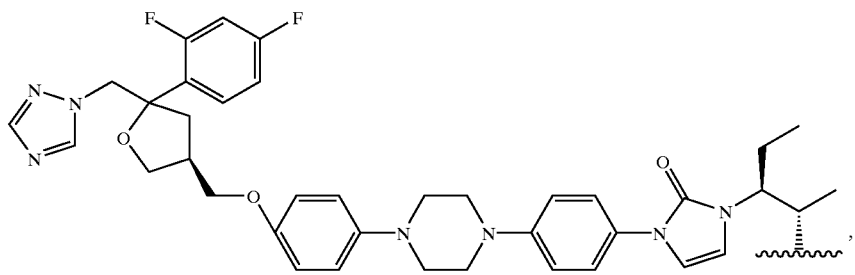

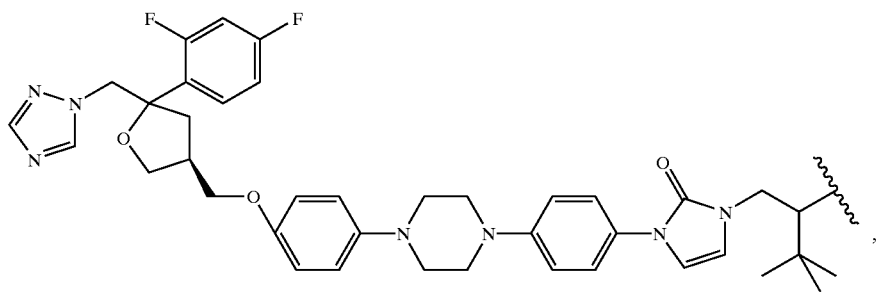

-continued

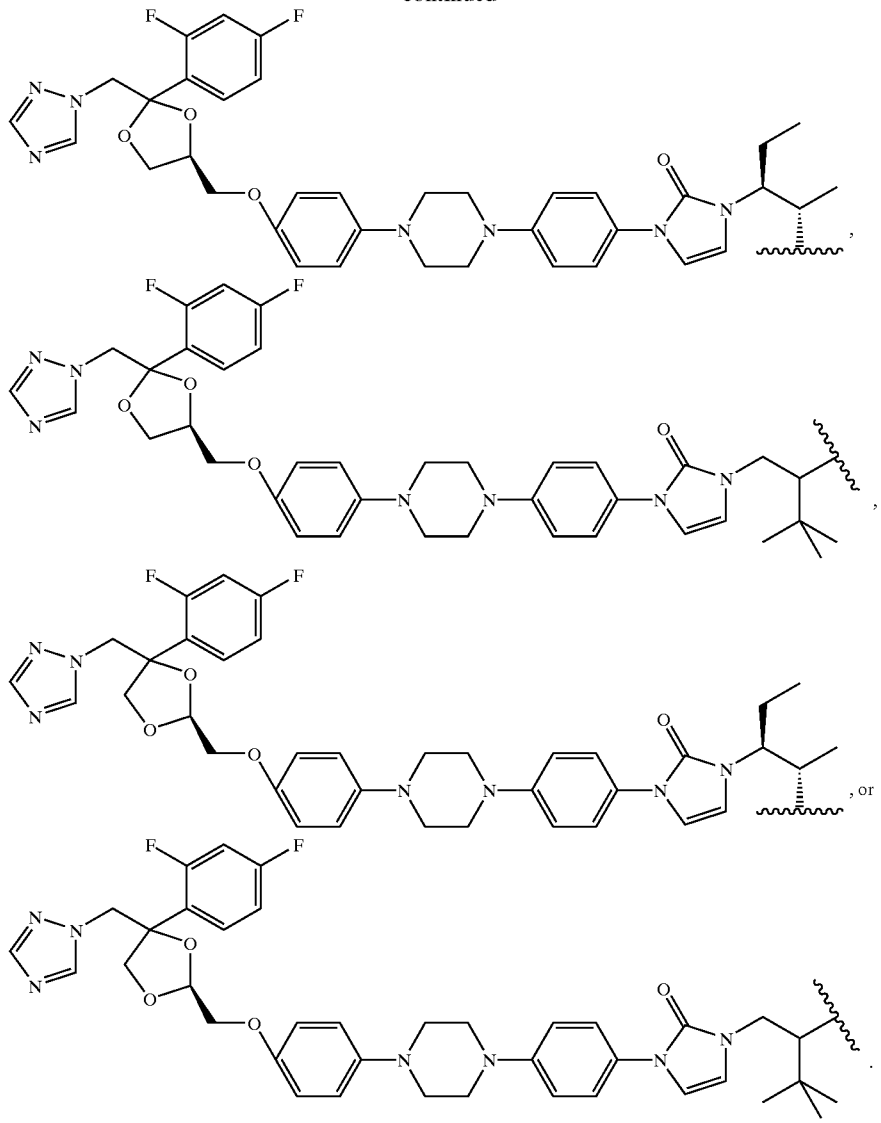

13. The compound named (2R,3R)-3-[4-(4-cyanophenyl) thiazol-2-yl]-2-(2,4-difluorophenyl)-1-(1H-1,2,4-triazol-1-yl)-2-[[[m[N,N-bis-(2-hydroxyethyl)aminomethyl] benzoyloxy]methoxy]carbonyloxy]butane, or a pharmaceutically acceptable salt thereof.

14. The compound named (2R,3R)-3-[4-(4-cyanophenyl) thiazol-2-yl]-2-(2,4-difluorophenyl)-1-(1H-1,2,4triazol-1-yl)-2-[[[m-[N,N-diethylaminomethyl]benzoyloxy]methoxy] carbonyloxy]butane, or a pharmaceutically acceptable salt thereof.

15. The compound named (2R,3R)-3-[4-(4-cyanophenyl) thiazol-2-yl]-20 2-(2,4difluorophenyl)-1-(1H-1,2,4-triazol-1-yl)-2-[[[m-[(4-(2'-hydroxyethoxy)ethyl]-piperazinyl) methyl]benzoyloxy]methoxy]carbonyloxy]butane, or a pharmaceutically acceptable salt thereof.

16. A method for the treatment of fungal infections, which comprises administering an effective antifungal amount of a compound of claim 1, or a pharmaceutically acceptable salt thereof, to a mammalian host in need thereof.

17. A pharmaceutical composition comprising a compound of claim 1, or a pharmaceutically acceptable salt thereof, in admixture with a pharmaceutically acceptable adjuvant, diluent, or carrier.

* * * * *